(12) United States Patent
Luk et al.

(10) Patent No.: US 11,614,407 B2
(45) Date of Patent: Mar. 28, 2023

(54) DEVICES FOR INSTANT DETECTION AND DISINFECTION OF AEROSOL DROPLET PARTICLES USING UV LIGHT SOURCES

(71) Applicant: Denovo Lighting, LLC, Flushing, NY (US)

(72) Inventors: John F Luk, Flushing, NY (US); Georgiana Hsu-Luk, Flushing, NY (US); Danielle Luk, Flushing, NY (US)

(73) Assignee: Denovo Lighting, LLC, Flushing, NY (US)

( * ) Notice: Subject to any disclaimer, the term of this patent is extended or adjusted under 35 U.S.C. 154(b) by 452 days.

(21) Appl. No.: 16/853,165

(22) Filed: Apr. 20, 2020

(65) Prior Publication Data

US 2020/0309703 A1    Oct. 1, 2020

(51) Int. Cl.
*A61L 2/24* (2006.01)
*G01N 21/64* (2006.01)
(Continued)

(52) U.S. Cl.
CPC ............ *G01N 21/6486* (2013.01); *A61L 2/10* (2013.01); *A61L 2/24* (2013.01); *G08B 3/10* (2013.01);
(Continued)

(58) Field of Classification Search
CPC .. G08B 3/10; G08B 21/12; A61L 2/24; A61L 2202/11; A61L 2202/14; G01N 21/6486;
(Continued)

(56) References Cited

U.S. PATENT DOCUMENTS

| | | |
|---|---|---|
| 2,650,672 A | 9/1953 | Barr et al. |
| 3,289,392 A | 12/1966 | Fowler |

(Continued)

FOREIGN PATENT DOCUMENTS

| | | |
|---|---|---|
| JP | 3503718 | 3/1996 |
| JP | H1190265 | 9/1997 |
| JP | 3650579 | 6/1999 |

OTHER PUBLICATIONS

Scientific Reports (2019) 9:12598 [https://doi.org/10.1038/S41598-019-49005-3] Entitled, "Laser-Nduced Fluorescence (LIF) as a Smart Method for Fast Environmental Virological Analyses: Validation On Picornavirus".

(Continued)

*Primary Examiner* — David P Porta
*Assistant Examiner* — Fani Polyzos Boosalis
(74) *Attorney, Agent, or Firm* — Fox Rothschild LLP; Carol E. Thorstad-Forsyth

(57) ABSTRACT

The present invention is directed to a device consisting of a portable and multi-band UV light device that uses a combination of UVA, UVB, and UVC wavelength band of UV emitters. For detection, UV emitters are energized to a particulate collector that will fluoresce and glow when there is the presence of a wide range of different harmful aerosol droplet particles in the air that may be collected. This instant and positive visual detection with an available audio alarm alert indicates the presence of harmful aerosol droplet particles in the vicinity of this Instant Particulate Detector or IPD device, allowing the user to take immediate and corrective action. The user can also subsequently select disinfection utilizing UVC wavelength light to sterilize the particulate collector and Instant Particulate Detector or IPD device.

65 Claims, 16 Drawing Sheets

(51) Int. Cl.
  *A61L 2/10* (2006.01)
  *G08B 21/12* (2006.01)
  *G08B 3/10* (2006.01)

(52) U.S. Cl.
  CPC ........... *G08B 21/12* (2013.01); *A61L 2202/11* (2013.01); *A61L 2202/14* (2013.01); *G01N 2201/0214* (2013.01); *G01N 2201/064* (2013.01); *G01N 2201/0628* (2013.01); *G01N 2201/0693* (2013.01)

(58) Field of Classification Search
  CPC ... G01N 2201/0214; G01N 2201/0628; G01N 2201/064; G01N 2201/0693
  See application file for complete search history.

(56) References Cited

U.S. PATENT DOCUMENTS

| | | | |
|---|---|---|---|
| 3,982,130 | A | 9/1976 | Trumble |
| 4,313,741 | A | 2/1982 | Masuda et al. |
| 5,466,279 | A | 11/1995 | Hattori et al. |
| 6,221,136 | B1 | 4/2001 | Liu et al. |
| 6,630,682 | B2 | 10/2003 | Shanley et al. |
| 7,564,365 | B2 | 7/2009 | Marman et al. |
| 8,118,899 | B2 | 2/2012 | Zhang et al. |
| 8,753,575 | B2 | 6/2014 | Neister |
| 8,804,119 | B2 | 8/2014 | Knox et al. |
| 8,946,662 | B2 | 2/2015 | Cooper et al. |
| 9,669,121 | B2 | 6/2017 | Liao et al. |
| 10,071,262 | B2 | 9/2018 | Randers-Pehrson et al. |
| 2021/0353969 | A1* | 11/2021 | Leschinsky ............... A62B 9/00 |
| 2021/0372637 | A1* | 12/2021 | Sharma ................... F24F 8/167 |

OTHER PUBLICATIONS

Scientific Reports [https://www.nature.com/S41598-018-21058-W] Entitled, "FAR-UVC Light: A New Tool To Control the Spread of Airborne-Mediated Microbial Diseases".

"Organic Ultraviolet Light Emitting Diodes" By Monica Katiyar, Asha Sharma, Deepak Department of Materials and Metallurgical Engineering & Samtel Center for Display Technologies Indian Institute of Technology Kanpur, India-208016 [Proc. of ASID '06, 8-12 Oct. New Delhi].

Scientific Reports (2019) 9:12598 [https://doi.org/10.1038/s41598-019-49005-3] Entitled, "Laser-Induced Fluorescence (LIF) as a Smart Method for Fast Environmental Virological Analyses: Validation On Picornavirus".

Scientific Reports [https://www.nature.com/articles/s41598-018-21058-w] Entitled, "Far-UVC Light: A New Tool To Control the Spread of Airborne-Mediated Microbial Diseases".

"Organic Ultraviolet Light Emitting Diodes" By Monica Katiyar, Asha Sharma, Deepak Department of Materials and Metallurgical Engineering & Samtel Center for Display Technologies Indian Institute of Technology Kanpur, India-208016 [Proc. of ASID '06, Oct. 8-12 New Delhi].

* cited by examiner

DEVICES FOR INSTANT DETECTION AND DISINFECTION OF AEROSOL DROPLET PARTICLES USING UV LIGHT SOURCES

FIELD OF THE INVENTION

The present invention relates to an instant detection device using different wavelengths of UV LED light to detect potentially dangerous particulates that may be present in the air that is initially collected onto a surface and may be subsequently disinfected. The present invention can be used in schools, hospitals, medical offices, clinics, homes, businesses, hotel rooms, rental cars, cruise ships, jet airliners, all public and private spaces, etc. where the presence of potentially dangerous particulates may be present by providing instant detection, and subsequent disinfection by the user for safety and to maintain health and well-being. This device provides instant detection of dangerous aerosol respiratory droplet particles including viral and bacterial microbe pathogens and smoke particulates, which are collected and will react to one or more UV excitation wavelengths for visual detection and confirmation.

BACKGROUND OF THE INVENTION

Around December 2019 and possibly earlier, the global widespread pandemic outbreak of the new SARS-COV-2 or coronavirus-19 that causes the COVID-19 disease has inflicted many individuals worldwide and has killed many others especially those with respiratory issues or those that are immunity compromised. In addition, in the USA the lack of readiness and availability of vital personal protection gear and life saving ventilators to help those inflicted with COVID-19 made containment of the spread of the disease challenging.

The main issue with this new and novel coronavirus is the long incubation period before a person having COVID-19 ever develop symptoms of this disease sometimes taking up to 14 days. Even with attempts at social distancing and stay at home mandates, some individuals are ignoring this and may have COVID-19 and continue to pass it around. This becomes dangerous for everyone, especially for the healthcare workers and first responders that work with both negative and confirmed positive COVID-19 inflicted individuals on a daily basis.

In the onset of the novel coronavirus outbreak, there was little or no testing available with earlier testing results only available in a few days to two weeks or more and sometimes coming in too late to save an infected patient's life or prevent the inflicted with proof-positive results from quarantining themselves or seeking professional medical assistance instant. While it is still unclear exactly how much of the current coronavirus outbreak has been fueled by asymptomatic, mildly symptomatic, pre-symptomatic, or fully symptomatic people, the risk is still there. That is because people who are asymptomatic can still spread the virus and have high levels of the virus in their respiratory secretions, and thus can rapidly spread COVID-19 by leaving harmful aerosol droplet particle transmissions in the air and on surfaces in areas they are in or have recently occupied from sneezing, coughing, breathing, and talking without wearing medical grade N95 type face masks.

Shortly, the FDA approved Abbott Lab's brand-new ID NOW blood testing provided a faster reporting for patients that may have contracted COVID-19 in as little as five minutes and can be done in a doctor's office. However, even with such instant result testing, there is no instant detection device for viral and bacterial particulates such as the COVID-19 virus and others including H1N1, MERS, SARS, etc. The present invention of an Instant Particulate Detector device that will instantly detect any signs of a virus microbial pathogen from respiratory aerosol droplet particles that may be lingering in the air from asymptomatic, mildly symptomatic, pre-symptomatic, and symptomatic people. Once these dangerous and harmful particulates are instantly detected, it will allow the user to conduct rapid response to the detection and perform immediate action to maintain personal health and well-being.

Coincidentally in November 2019, there had been an increasing number of cases involving electronic vaping users getting sick and some dying from holes in their lungs caused by vaping. Doctors called this EVALI or Electronic Vaping Lung Injury or "popcorn lungs". The term "popcorn lung" is the term for bronchiolitis obliterans, a type of lung disease where the tiniest airways called bronchioles are inflamed. Recent research also found that exposure to e-cigarette vapor can impair the lung's ability to fight viral infections like the flu and other viruses.

There now becomes a need for an immediate and instant particulate detector and warning device that can always help keep the general public safe and healthy and notifying persons of such possible exposures that can hurt individuals alike.

The present invention which we will call an Instant Particulate Detector or IPD provides a user instant detection of possible deadly particles that may be in the air in the immediate vicinity of the user. The device uses UV light to initially fluoresce particulates in the air, and then provides subsequent disinfection of the collected particulates at the option of the user allowing the device can be reused and continues to monitor.

Articles for using UV light to detect bacterial and viral particulates include a Scientific Reports (2019) 9:12598 [https://doi.org/10.1038/s41598-019-49005-3] entitled, "Laser-induced fluorescence (LIF) as a smart method for fast environmental virological analyses: validation on Picornavirus". The report discloses experimental tests were performed in which different viruses were irradiated with a UV laser emitting at 266 nm and the emitted spectra were recorded by a spectrometer. By irradiating the sample with UV light, some molecules absorb and re-emit less energetic radiation (visible region). This phenomenon is called fluorescence, and the spectrum emitted is a function of the specific molecules compounding the microorganisms. The article states the fluorescence light ranges from 350 nm to 700 nm.

There is also a document describing the use of 222 nm wavelength UVC for efficiently inactivating airborne aerosolized viruses. In the constant battle against the spread of infectious diseases, scientists are continually on the hunt for new weapons that specifically target pathogenic microbes. Now, investigators from the Center for Radiological Research at Columbia University Irving Medical Center (CUIMC) believe they may have found a new, low-cost solution to eradicating airborne viruses in indoor public spaces. The research team found that continuous low doses of far ultraviolet C (far-UVC) light can kill airborne flu viruses without harming human tissues. The findings from the new study—published in Scientific Reports in an article entitled, "Far-UVC Light: A New Tool to Control the Spread of Airborne-Mediated Microbial Diseases [https://www.nature.com/articles/s41598-018-21058-w]" suggests that use overhead far-UVC light in hospitals, doctor's offices, schools, airports, airplanes, and other public spaces could provide a powerful check on seasonal influenza epidemics, as well as influenza pandemics. Scientists have known for decades that broad-spectrum UVC light, which has a wavelength of between 200-400 nm, is highly effective at killing bacteria and viruses by destroying the molecular bonds that hold their DNA together. Unfortunately, conventional germicidal UV light is also a human health hazard and can lead to skin cancer and cataracts, which prevents its use in public spaces. However, a narrow spectrum of ultraviolet light called far-UVC could kill microbes without damaging healthy tissues. Far-UVC light has a very limited range and cannot penetrate through the outer dead-cell layer of human skin or the tear layer in the eye, so it is not a human health hazard. They found that far-UVC light at very low does of 222 nm far-UVC light efficiently inactivated the H1N1 flu viruses with about the same efficiency as conventional germicidal UV light. The authors state the continuous very low dose-rate far-UVC light in indoor public locations is a promising, safe, and inexpensive tool to reduce the spread of airborne-mediated microbial diseases.

Lastly, there is an article disclosing the use of OLEDs to provide UV Light. It is entitled, "Organic Ultraviolet Light Emitting Diodes" by Monica Katiyar, Asha Sharma, Deepak Department of Materials and Metallurgical Engineering & Samtel Center for Display Technologies Indian Institute of Technology Kanpur, India-208016 [Proc. Of ASID '06, 8-12 October New Delhi]. In it they disclose that highly efficient organic light emitting diodes have been developed for almost all wavelengths of visible spectrum. It is natural to extend the available emissions to ultraviolet region. Polysilanes are candidate materials for emission in ultraviolet and near-ultraviolet. Electroluminescence (EL) devices using polysilanes show highest normalized intensity at 357 nm wavelengths. This is important as EL with UV emissions in UV-NUV ranges can be used as embodiments in the present Instant Particulate Detector or IPD invention device.

An organic light-emitting diode or OLED is also known as an organic EL or organic electroluminescent (EL) diode in which the emissive electroluminescent EL layer is a film of organic compound that emits light in response to an electric current. The basic structure of an OLED is an emissive layer sandwiched between a cathode (which injects electrons) and an anode (which removes electrons). Modern OLED devices use many more layers in order to make them more layers in order to make them more efficient and durable. The main structure of an OLED device includes a back reflector substrate, anode, hole injection layer (HIL), hole transport layer (HTL), emissive layer, blocking layer (BL), electron transport layer (ETL), and cathode. Some alternate constructions of different embodiments of the present invention use UV OLEDs as the main source of UV light used in the IPD devices.

For the disinfection of dangerous bacterial and viral particulates, there are some patents that use UV light at 254 nm and safer 222 nm wavelengths for sterilization purposes only, but none are specifically for the instant detection of dangerous vapor, bacterial, or viral particulates with the additional and subsequent optional disinfection using UVC in the range from 200 nm to 280 nm. Most recently UVC LEDs are presently available in 250 nm and 275 nm wavelengths for disinfection and germicidal purposes.

U.S. Pat. No. 8,753,575 issued to Neister on Jun. 17, 2014 entitled, "Method and Apparatus for Sterilization and Disinfecting Air and Surfaces and Protecting a Zone from External Microbial Contamination" discloses a method, process and apparatus for disinfecting and sterilizing all types of surfaces contaminated with microorganisms and toxic substances to render both inactive. The apparatus consists of a new ultraviolet (NUV) source that is more effective tan mercury based 254 nm for destroying DNA of virus, bacteria, spores and cists. Critical to this method is the development of a new ultraviolet (NUV) source that emits single line photons that correspond to the maximum absorption band for DNA. The preferred embodiment is a NUV source at 222 nm. This spectral emission is 10,000 times more effective than standard 254 nm photons for stopping DNA replication. This patent method and apparatus focuses mainly on the sterilizing and disinfecting of air and surfaces, but it does not disclose an active and instant detection device like the present invention.

U.S. Pat. No. 8,946,662 issued to Cooper et al. on Feb. 3, 2015 entitled, "Excimer Light Source" discloses a light source with electrodes of alternating polarity attached to a substrate in an excimer ultraviolet (UV) lamp for generating a plasma discharge between each of the electrodes. The UV excimer lamp of this patent produces light having a wavelength in a range of 100 nm to 400 nm in one embodiment; and where the gas discharge light source produces light having a wavelength of about 222 nm. This patent describes the use of a UV light and more specifically an excimer lamp gas discharge light source generating the full UV range of wavelengths from 100 nm to 400 nm from one light source including 222 nm. The present invention of the IPD uses multiple UV light sources to first detect dangerous particulates, and then offers the option to disinfect the particulates using only one of the UVC range of 200 nm to 280 nm or discrete peak wavelengths of 254 nm or safer 222 nm, or presently with available 250 nm and 275 nm.

U.S. Pat. No. 10,071,262 issued to Randers-Pehrson et al. on Sep. 11, 2018 entitled, "Apparatus, method, and system for selectively effecting and/or killing bacteria" discloses an apparatus and method for selectively killing and/or affecting at least one bacterium. The at least one radiation having one or more wavelengths provided in a safe range of about 190 nm to about 230 nm. In certain exemplary embodiments of the present disclosure, a UV irradiator, e.g. the KrBr (Krypton Bromide) and KrCl (Krypton Chloride) excilamps, can be provided which can affect and/or kill bacteria without being harmful to human cells. The exemplary system, method and apparatus takes into consideration that bacteria are typically and physically much smaller than human cells, and thus, an appropriately chose UV wavelength (e.g. around 207 nm to 220 nm) preferably penetrates and kills bacteria, but preferably would not be able to penetrate into the biologically sensitive nucleus of human cells. According to further exemplary embodiments of the present disclosure, it is possible to provide exemplary UV lamps that can emit at a single wavelength, in contrast to standard mercury UV lamps which typically emit over a wide range of wavelengths. The single wavelength can be about 206 nm, 207 nm, and/or 222 nm. Once again, this patent describes the use of a UV light and more specifically an excimer lamp gas discharge light source generating UV light in the range of 190 nm to 230 nm wavelengths and including peak wavelength of 207 nm or 222 nm. In contrast, the present invention of the IPD uses multiple UV light sources to first detect dangerous particulates in the entire range from 200 nm to 400 nm, and then offers the option to disinfect the particulates using only one of the UVC range of 200 nm to 280 nm or discrete peak wavelengths of 254 nm or safe 222 nm, or presently with available 250 nm and 275 nm.

Now for detecting dangerous smoke vapor and similar particulates, there are many patents that address various methods and UV light sources for improved smoke particulate detectors, but no patent involves the use of an Instant Particulate Detector (IPD) device and a smoke particulate collector in the same apparatus for the sole purpose of verifying an act of vape smoke particulates are present. U.S. Pat. No. 3,982,130 issued to Trumble on Sep. 21, 1976 entitled, "Ultraviolet Wavelength Smoke Detector" discloses a smoke detector that uses specifically two different UV wavelengths, and where the two wavelengths are dimensionally shorter than the smoke particle diameters that are being detected. The present invention uses all three different UV wavelength ranges to detect a wider band of smoke particulates from various types of smoking devices and materials for instant detection.

U.S. Pat. No. 6,630,682 issued to Shanley et al. on Oct. 7, 2003 entitled, "Combination UV Inspection Light and Flashlight" discloses a light that combines two different light sources consisting of a UV LED light source with a full spectrum white light source. For example, the UV LED light source has a wavelength in the UVA band range from 350 nm to 450 nm in combination with a full spectrum white light source with wavelengths greater than 450 nm, or the UV LED light source has a wavelength in the UVB band range from 320 nm to 380 nm in combination with a full spectrum white light source with wavelengths greater than 400 nm. In contrast, the present invention uses a combination of all three types of UV LEDs in multiple UV wavelength band ranges of UVA, UVB, and UVC light with no other wavelengths of light greater than 450 nm.

U.S. Pat. No. 7,564,365 issued to Marman et al. on Jul. 21, 2009 entitled, "Smoke Detection and Method of Detecting Smoke" discloses a smoke detector having a first light source emitting light to a target area in a first wavelength range, and a second light source emitting light to a different target area in a second wavelength range. The first wavelength range can be in the infra-red wavelength range and is different from the second wavelength range that can be in the ultra-violet wavelength range. The present invention uses a combination of all three types of UV LEDs in multiple UV wavelength band ranges of UVA, UVB, and UVC light with no IR wavelengths. All UV LED light from the three types of Instant Particulate Detector IPD device output bands are projected to the same target area for the detection of any smoke particulates that may be present in a particulate collector.

U.S. Pat. No. 8,804,119 issued to Knox et al. on Aug. 12, 2014 entitled, "Particle Detection" discloses a system with one or more of light emitters adapted to emit light at a respective wavelength, and wherein a light source is configured to illuminate the volume being monitored at each of the at least two wavelengths at different times. The present invention uses a combination of all three types of UV LEDs in multiple UV wavelength band ranges of UVA, UVB, and UVC light that are all energized at the same time to the same target area for the detection of any smoke particulates that may be present in a particulate collector.

Lastly, U.S. Pat. No. 9,669,121 issued to Liao et al. on Jun. 6, 2017 entitled, "Ultraviolet Light Source and Methods" discloses a method for a hand-held device that firstly illuminates an object surface with a first UV LED, and secondly illuminates the same object surface with a second UV LED after some internal calculations and user selection is made. The first UV LED is within the UVA band, and the second UV LED is within the UVC band. The present invention uses a combination of all three types of UV LEDs in multiple UV wavelength band ranges of UVA, UVB, and UVC light that may be all energized at the same time to the same target area for the detection of any smoke particulates that may be present in a particulate collector.

Other related patents like U.S. Pat. No. 6,221,136 issued to Liu et al. on Apr. 24, 2001 entitled, "Compact Electro static Precipitator for Droplet Aerosol Collection"; U.S. Pat. No. 3,289,392 issued to Fowler on Dec. 6, 1966 entitled, "Collector Cell Housing for Electrostatic Precipitator"; U.S. Pat. No. 2,650,672 issued to Barr et al. on Sep. 1, 1953 entitled, "Electrostatic Precipitator"; JP3,650,579 entitled, "Film Type Electrostatic Precipitator"; JP 3,503,718 entitled, "Dust Collecting Electrode Coated of the Electrostatic Precipitator and its Dust Collecting Electrode"; JPH 1,190,265 entitled, "Electric Dust-Collecting Filter"; U.S. Pat. No. 4,313,741 issued to Masuda et al. on Feb. 2, 1982 entitled, "Electric Dust Collector"; U.S. Pat. No. 5,466,279 issued to Hattori et al. on Nov. 14, 1995 entitled, "Electric Dust Collector System"; and U.S. Pat. No. 8,118,899 issued to Zhang et al. on Feb. 21, 2012 entitled, "Self-Cleaning Device of Filtering Net of Air Conditioner"; are some inventions that include electrostatic precipitators or film type dust collectors for use in particulate collectors.

Based on the above disclosures, it is the objective of this invention to provide an instant detector of dangerous particulates and enable countermeasures to be taken immediately. Electronic cigarette smoke vapors consisting of polycyclic aromatic hydrocarbons fluoresce at 370 nm to 490 nm (UVA-UVB) and propylene glycol with vegetable glycerin fluoresce at 300 nm to 450 nm (UVA-UVB). In addition, fluorescent detection of viral pathogens occurring from 200 nm-700 nm (UVA-UVB-UVC) with peak wavelengths at about 590 nm to 530 nm. Subsequently, the IPD will provide detection by using all wavelengths of UV light including UVA from 400-315 nm; UVB from 315-280 nm; and UVC from 280-200 nm. The IPD can then include automatic disinfection using only UVC in the range of 190 nm to 280 nm based on a timer and sensor feedback; or by manual detection and disinfection based on user input. UVC wavelengths with peaks at 254 nm (UVC), or at the safer 222 nm (UVC) may be used by the IPD device for the subsequent germicidal disinfection and sterilization purposes.

There becomes an apparent and immediate need for such a device that will collect, detect, and disinfect any number of dangerous droplet particulates that may be found in any confined space and environment. The device will detect different types of bacterial and viral particulates including influenza and the novel coronavirus-19 or any new virus that may come into existence, as well as any type of potentially dangerous smoke particulates from e-cigarette vapors, etc. The primary device incorporates a built-in Instant Particulate Detector (IPD) using particulate collector, the combination of which can be instantly activated to show the presence of dangerous particulates collected in the immediate vicinity of the IPD device, and allowing the user the decision to take corrective measures including vacating the premises, getting a blood test, cleaning the space, etc.

The combination Instant Particulate Detector (IPD) and particulate collector can be used to collect and detect all types of bacterial and viral pathogens with peak wavelengths in the range of about 490 nm to 530 nm with fluorescence in the range of 200 nm to 700 nm. This includes all types of fungus spores with sizes in the range of about 15.00 microns to 2.50 microns; bacteria in the size range of about 10.00 microns to 0.10 microns; and viruses in the size range from about 0.100 microns to 0.01 microns. The COVID-19 coronavirus measures between 0.05 and 0.20 microns.

The electromagnetic spectrum of ultraviolet UV light can be subdivided in several ways. The draft ISO standard on determining solar irradiances (ISO-DIS-21348) describes the UVA (400~315 nm), NUV (400~300 nm), UVB (315~280 nm), MUV (300~200 nm), and UVC (280~100 nm).

The combination Instant Particulate Detector (IPD) and particulate collector can also be used to collect and detect all smoking chemical components that have UV excitation wavelengths in the following ranges:

Nicotine (all 4 major forms)—220 nm to 280 nm
Tar—400 nm
THC (all 3 major forms)—220 nm to 300 nm
Polycyclic aromatic hydrocarbons—370 nm to 490 nm
Propylene glycol and/or vegetable glycerin (Humectants)—300 nm to 450 nm.

The built-in and integral Instant Particulate Detector (IPD) device for detecting one or more of the different types of smoking chemical components works in conjunction with the particulate collector. The detection of smoke particles may therefore be through classic excitation fluorescence using the Instant Particulate Detector (IPD) device with the following UV wavelength ranges:

UVA—400 nm to 315 nm
UVB—315 nm to 280 nm
UVC—280 nm to 200 nm

The Instant Particulate Detector (IPD) device when activated will fluoresce the contents in the particulate collector when any smoking chemical component is present and collected on the particulate collector to indicate the presence of smoke particulates.

The present invention of the preferred embodiment therefore includes a built-in and integral Instant Particulate Detector (IPD) device for instant detection contains at least one UV LED emitter each that emits wavelengths in the UVA, UVB, and UVC frequency in the range about 100 nm to 400 nm installed in the same Instant Particulate Detector (IPD) device. UVA and UVB and UVC LED emitters are all activated at the same time for instant detection. The activation of the different types of Instant Particulate Detector (IPD) device will provide a general indication that harmful particulates may be in the general vicinity of the IPD device. The quickest and fastest confirmation testing is to then to have all the UVA, UVB, and UVC LED emitters turned on at the same time to detect the widest range and confirm if any smoke or microbial pathogens may be collected and detected in the particulate collector of the IPD device.

There is also a need for an instant alert detector for harmful particulates that can be used during an Emergency pandemic and during Non-Emergency daily use for an active and instant warning detector of harmful particulates that can be present.

The IPD device will help to reduce and eliminate the fear of first responders and healthcare workers in the front line that handle and take care of possibly inflict patients that have contracted the dangerous and sometimes deadly airborne particle droplets.

The IPD device can be used during the COVID-19 outbreak pandemic, or to monitor and detect any future outbreaks of viral and bacterial microbial pathogens that may be in the air.

Lastly, the IPD device of the present invention has an option for a built-in germicidal cleaning function to disinfect and sterilize the IPD device after detection and allow the unit to be reused repeatedly. The process is dry and will not necessitate the IPD device to be sprayed and wet-down from disinfection or germicidal spraying saving on wet wipes and additional use of cleaning sprays and liquids and wipes.

In addition, the demand for PPE or Personal protective equipment far exceeding the supply of the protective gear in some instances can have the IPD device incorporated into the PPE and can easily disinfect existing and used protective gear for immediate reuse, thereby extending the life of the valuable and necessary protective gear, and also providing a green solution to save on unnecessary waste and added littering.

SUMMARY OF THE INVENTION

The subject invention consists of a portable and battery operated IPD device having one or a plurality of UV LED emitters outputting at the UVA, UVB, and UVC wavelength bands towards a particulate collector. The particulate collector is made primarily of a plastic or glass lens cover that substantially allows UV light to pass through against a background reflector to reflect any stray UV light outward for better display of any fluorescent particulates. A dark or black background reflector is the best choice for contrast and visibility of the fluorescent particles through the particulate collector. In more detail of the preferred embodiment of the present invention, the IPD device consists of many parts. The IPD device is constructed of a back frame housing, background reflector, edge-lit UV LED circuit board light bar, light guide panel, particulate collector, front frame housing, power supply unit, rechargeable battery, LED control electronics, and power and selector switch. The entire IPD device of the present invention is designed to be worn by a user like a badge fastened to the chest, hung as a pendant around the neck on a lanyard, or around the arm in a shoulder holster holder all of which will allow the user to be able to easily glance at the front of the IPD device for a visual detection. When any harmful particulates are collected on the front exposed particulate collector of the IPD device, the particulates will glow brightly from the UV light fluoresces the particulates against the background reflector light indicating the presence of dangerous particulates in the immediate vicinity of the IPD device. The UV LED emitters are arranged on the edge or around the periphery of the light guide panel with the light from the UV LED emitters all pointed to the center of the light guide panel between the background reflector plate and the front diffuser plate and plastic or glass particulate collector. An alternating arrangement of each UVA LED emitter, UVB LED emitter, UVC LED emitter, etc. would provide for a more diffused and even distribution of the UV LED emitted light rays resulting in a more even glow or fluorescents of the droplet particulates collected on the particulate collector for viewing. At least one tiny light sensor can be mounted to the center of the particulate collector that will activate an audible warning alarm like a small piezo when the detector has a positive detection of glowing particulates in collected in the particulate collector. The use of both visual and audio detection helps to provide instant detection of harmful particulates in the air and gives the user advance notice to take corrective actions.

The IPD device of the present invention performs multiple functions including the collection and detection, but it can also allow for the disinfection of harmful particulates that may be present in any immediate environment.

Collection is done by a particulate collector mounted inside the IPD device that may include a piece of plastic or glass for capturing and collecting droplet particulates in the air. Or it can simply collect any airborne droplet particulates by electrostatic and gravitational adhesion forces that may naturally be found on thin plastic or glass lens collector cover.

Detection is done in the IPD device with UV light containing all wavelengths of UVA, UVB, and UVC in the range from about 190 nm to 400 nm, all energized at the same time to fluorescence any particulates that may be collected on the particulate collector. If the particulate collector fluoresces at any time with the multi-band UV light Instant Particulate Detector IPD device, then there is a positive confirmation that there are harmful particulates in the immediate environmental space where the IPD device and particulate collector is immediately located. Once detection is proved positive, the IPD device may also produce an audible alarm to alert the user a harmful particulate was detected. The user will then take immediate action including vacating the contaminated space to a safe distance farther away from the present detection, perform immediate disinfection and sterilization of the immediate environmental space, get actual virus blood test done, etc.

After the user of the IPD device has taken the necessary precautions, they can then activate the IPD device to initiate the disinfection and sterilization of the particulate collector using only UVC germicidal wavelengths in the range from 190 nm to 280 nm, so that the IPD device can be reused and placed back into the detection mode. It is recommended the IPD be placed inside a sealable container to allow the UVC light to illuminate the entire IPD device including the internal particulate collector. As part of the routine maintenance routine, the user should regularly disinfect the IPD device and all other PPE manually by using germicidal wipes and sprays for germ-free cleanliness and personal safety.

It then becomes a first object of this invention to introduce an instant and simple device to confirm the presence of harmful particulates in the vicinity of the Instant Particulate Detector IPD device.

It is another object of this invention to incorporate a combination of UV LED emitters in which at least one first UV LED emitter outputs in the UVA range wavelength band, at least one second UV LED emitter outputs in the UVB range wavelength band, and at least one third UV LED emitter outputs in the UVC range wavelength band, all UV LED emitters are to be energized together at the same time to the same target particulate collector object area for the instant detection of harmful particulates that may be collected as droplets in the air.

It is yet another object of this invention to provide a complete Instant Particulate Detector (IPD) device in the wavelength range from 190 nm to 400 nm inclusively containing all wavelengths in the UVA, UVB, and UVC wavelength band ranges for detection purposes.

It is another object of this invention to allow the users of the present IPD invention to activate the disinfection of the IPD device using UVC light.

It is a final object of this invention to easily incorporate the IPD device to existing Personal protective equipment PPE including but not limited to safety glasses and eye goggles, face masks, face shields, safety gloves, arm sleeves, head hoods, solid hairnets, body coveralls, body gowns, aprons, and other protective gear, etc.

A power switch is used to power up the multi-band UV light Instant Particulate Detector IPD device whose primary operation is to turn on all three types of UV LED emitters consisting of one or more of UVA, UVB, and UVC each in their respective wavelength band ranges. The power switch can be a simple ON/OFF switch that will send power from internal rechargeable battery located inside the Instant Particulate Detector IPD device directly to the UV LED emitters when the power switch is activated. It can also be a 3-position slide-type switch for OFF, DETECT, or DISINFECT modes. Or, the IPD may incorporate two separate switches, one for ON/OFF and the second for DETECT/DISINFECT modes. The Instant Particulate Detector may also contain built-in automatic modes including automatic disinfection times, or flashing LEDs to warn of low battery status, charging status, as well as audible alarms for detection of harmful particulates collected, or for low battery status alerting the user to recharge the IPD device soon for maximum protection and monitoring.

As an additional configuration, the power switch can be the type of 3-way switch in subsequent pushes of the one button can turn off the IPD, place the IPD in DETECTION mode, or place the IPD in DISINFECTION mode. Pushing the button one more time turns the IPD off again. In DETECTION mode, all UV LED emitters are energized, and an optional audio alert may sound if any particulates are collected in the particulate collector of the IPD device. In DISINFECTION mode, only the UVC LED emitters are energized. If the IPD is not turned off or back to the DETECTION mode after a period of at least 15 minutes, the IPD device will automatically turn off to conserve battery life and any residual battery charge available for the IPD device remain in optimum use and performance.

Now the Instant Particulate Detector IPD device of the present invention can be incorporated into many embodiments. Some embodiments allow the IPD device to operate as a separate and standalone device to be used alongside other protective gear, or other embodiments of the IPD device can be adapted to fit into existing PPE and work together to allow for the same instant detection of harmful particulates that may be present in the immediate vicinity of the PPE equipment and will allow the user to take appropriate action. The IPD device can be made to be rechargeable with an audio alert or the Instant Particulate Detector device can be made at a low cost with replaceable batteries.

In one embodiment, the multi-band UV light Instant Particulate Detector IPD device is a portable and standalone IPD device like a badge or pendant. The portable Instant Particulate Detector (IPD) is compact and consists of a front UV LED emitter housing containing at least one each of a UVA, UVB, and UVC LED emitter mounted onto a circuit board. There is a lens made of acrylic plastic or quartz glass cover that will not absorb but will transmit all UV wavelengths of light. It is a particulate collector and will also serve as a protective barrier to prevent damage to the UV LED emitters and will help keep the UV LED emitters free from dirt and dust. The UV LED emitters are edge mounted against a preferably dark contrasting background reflector with the UV light pointed inwards toward the particulate collector through an optional Light Guide Panel (LGP) that will take the UV light and redirect it 90 degrees out the front of the IPD device. The LGP can be eliminated if side-emitting UV LED emitters are used. An alternating arrangement of each UVA LED emitter, UVB LED emitter, UVC LED emitter, etc. would provide for a more diffused and even distribution of the UV LED light rays resulting in a more even glow or fluorescents of the droplet particulates collected on the particulate collector for viewing. An alternate configuration would be to use at least one electroluminescent UV OLED as the UV light source instead of using UV LED emitters with each UV OLED sharing a single dark contrasting substrate background reflector. In the back-rear section of the portable Instant Particulate Detector (IPD) is the battery compartment, power switch mechanism, and related electronics to deliver power from the rechargeable or replaceable batteries to energize the UV LED emitters when the power switch is activated. These round IPD devices can be called Instant Particulate Detector Dots or IPDD. Lastly, an optional hanging strap is provided on the portable Instant Particulate Detector (IPD) for the user to wear the device around the neck. In lieu of the strap, the IPD device can include an adhesive strip or magnets, etc. to attach the IPD device to clothing or a gown, or a shoulder arm strap and holder can be provided to allow the IPD device to be worn around the upper arm bicep area for quick visibility of the front of the IPD device.

In another embodiment, the multi-band UV light Instant Particulate Detector IPD device is a portable and lightweight IPD strip with adhesive backing or reusable Velcro type attachments. The portable Instant Particulate Detector (IPD) strip is flexible and can be applied to existing PPE gear including goggles, face masks, face shields, gloves, cap, gowns, etc. The flexible IPD strip consists of at least one each of a UVA, UVB, and UVC LED emitter mounted onto a flexible linear bezel tape circuit board. An alternating and densely packed linear arrangement of each UVA LED emitter, UVB LED emitter, UVC LED emitter, etc. would provide for a more diffused and evenly distributed of the UV LED emitted light rays resulting in a more even glow or fluorescents of the droplet particulates collected on the particulate collector for viewing. The particulate collector is a silicone lens covering over the entire length of the flexible linear bezel LED tape circuit board that will transmit all UV wavelengths of light through it. The silicone covering lens will also serve as a protective barrier to prevent damage to the UV LED emitters and will help keep the UV LED emitters free from dirt and dust. The polyimide material flexible circuit board will have a dark outer layer background reflector to reflect any stray UV light for best contrast. The UV LED emitters mounted in front of the preferably dark contrasting background reflector with the UV light pointed outward towards the silicone lens cover serving as the particulate collector of this IPD embodiment. An alternate configuration would be to use an electroluminescent UV OLEDs as the UV light source instead of using UV LED emitters and preferably against a dark contrasting background substrate reflector. In one end section of the portable Instant Particulate Detector (IPD) will be the rechargeable or replaceable battery compartment, power switches, and related electronics to deliver power from the rechargeable or replaceable battery to energize the UV LED emitters when the power switch is activated. This IPD strip can be cut to length to fit onto most all sizes of different PPE gear for the best versatility and wide use by everyone. Audio alerting can also be implemented in this embodiment.

In yet another embodiment of the present invention, low cost electroluminescent UVABC OLED based instant particulate detector IPD devices without disinfection means can be made in the shape of compact circular DOTS or in small rectangular STRIPS that can use replaceable button type batteries can be made quickly and in mass production.

In a final embodiment of the present invention, the multi-band UV light Instant Particulate Detector IPD device can be implemented into a large size container box with a lid and window in which Personal Protective Equipment or PPE gear and other objects like bags, mail, shoes, keys, etc. that may also be exposed to harmful particulates can be put in the box, the DETECTOR can be energized to inspect the articles for infection, and then the user can choose DISINFECTION to sterilize the infected articles using UVC. Subsequent activation of the DETECTOR mode can verify the contents are germ-free and no longer present a danger.

These and other aspects, features, and advantages of the present invention will become more readily apparent from the following attached drawings and the detailed description of the preferred and alternate embodiments.

BRIEF DESCRIPTION OF THE DRAWINGS

The preferred and alternate embodiments of the present invention will be described in conjunction with the appended drawings provided to illustrate and not to the limit the invention, where like designations denote like elements, and in which.

DETAILED DESCRIPTION

Figure 1:
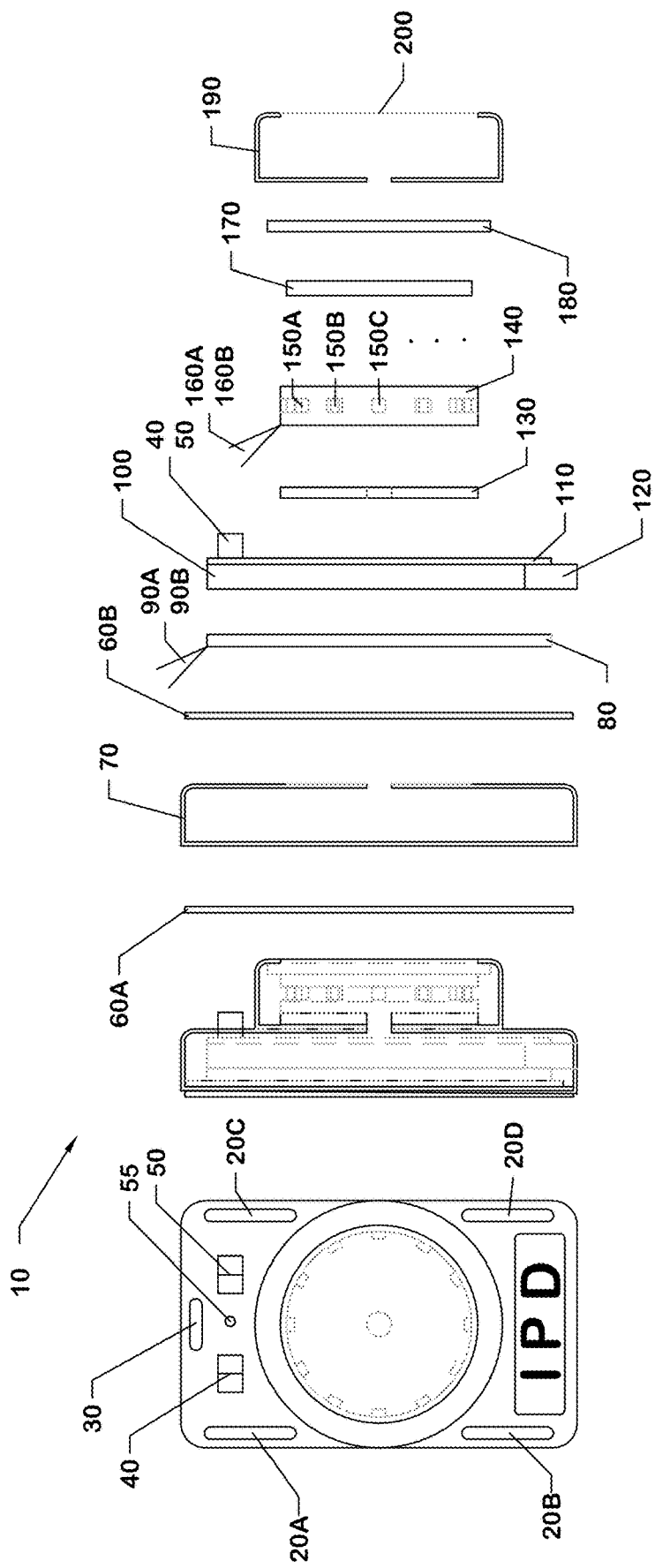
FIG. 1 shows a front and side views and assembly view of a preferred first embodiment of a multi-band UV light Instant Particulate Detector (IPD) device using at least one each of a UVA, UVB, and UVC LED emitters as the UV light source arranged in a periphery within a housing including other components to be used as a standalone Instant Particulate Detector device.

FIG. 1 shows full front and side views and assembly view of a preferred first embodiment of a multi-band UV light Instant Particulate Detector (IPD) device 10 using at least one each of a UVA LED emitter 150A, UVB LED emitter 150B, and UVC LED emitter 150C are the UV light sources arranged in a periphery within a front housing 190 including other components to be used as a standalone Instant Particulate Detector device 10. IPD device 10 includes passageway slots 20A, 20B, 20C, and 20D for straps (not shown), so that IPD device 10 can be worn on the upper arm of a user. A top passageway slot 30 is also provided for use with a lanyard or neck strap (not shown) if the user decides to wear the IPD device 10 around the neck. IPD device 10 can then be used as a name badge or hanging pendant. Both methods of hanging IPD device 10 will allow the user to easily view the front opening 200 of IPD device 10.

Power switch 40 allows IPD device 10 to be turned ON or OFF manually by a user, and mode select switch 50 allows the user to manually set the IPD device 10 in DETECTION mode or in DISINFECTION mode. In the DETECTION mode setting, at least one UVA LED emitter 150A, at least one UVB LED emitter 150B, and at least one UVC LED emitter 150C are all energized at the same time. In the DISINFECTION mode setting, at least one UVC LED emitter 150C is energized only. The at least one UVA LED emitter 150A and at least one UVB LED emitter 150B remain off. Speaker hole 55 is optional and is triggered by a small light sensor (not shown) to provide an additional audio alarm alert to supplement the visual instant detection front opening 200 of the IPD device 10. Lastly, there is a section marked "IPD" that can be used to display any logo to help identify IPD device 10.

Moving on to the next component in IPD device 10 is a thin double-sided adhesive strip 60A serving as yet another method for attaching IPD device 10 to a smooth flat surface and to temporarily mount the IPD device 10 to a wall or smooth flat surface (not shown). In some instances, thin double-sided adhesive strip 60A can be a thin steel metal plate with one-sided adhesive for attaching the thin steel metal back plate to the back of rear housing 70 of IPD device 10. This will allow IPD device 10 to be used with commercially available magnetic mounts (not shown) for holding IPD device 10 in place as a stationary instant particulate detector IPD device 10 for use in a room or vehicle, etc.

Rear housing 70 of IPD device 10 is preferably made of lightweight and durable plastic. Rear housing 70 contains thin double-sided adhesive strip 60B, battery 80, and LED control electronics 100 and printed circuit board 110. Battery 80 is a thin and low profile Lithium-Ion rechargeable type battery like LiPo or Lithium Polymer with a positive lead 90A and a negative lead 90B that connects to LED control electronics 100 and printed circuit board 110. Switches 40 and 50 are connected to and are part of LED control electronics 100 and printed circuit board 110. USB charging port 120 is provided and is also part of the LED control electronics 100 and printed circuit board 110 to charge battery 80. LED control electronics 100 also contains an IC controller and driver (not shown) that supplies power to UV LED emitters 150A, 150B, and 150C preferably with a constant current. When a charging cable (not shown) is connected to USB charging port 120, the IPD device 10 is powered by the USB charger (not shown) that also charges battery 80. When the IPD device 10 is removed from the USB charger (not shown), battery 80 powers the IPD device 10.

Front housing 190 of IPD device 10 is also preferably made of lightweight and durable plastic and attaches to rear housing 70 by attachment means (not shown). Front housing 190 contains back reflector 130, LED circuit board 140 with positive wire lead 160A and negative wire lead 160B, at least one UVA LED emitter 150A, at least one UVB LED emitter 150B, at least one UVC LED emitter 150C, optional light guide panel (LGP) 170, and particulate collector 180. Back reflector 130 is located behind LGP 170 and the UV LED emitters 150A, 150B, and 150C. It uses a reflective surface material and preferably has a dark or black background color to reflect any stray UV light outward to fluoresce and glow particulates collected on particulate collector 180. Particulate collector 180 can be made of PMMA acrylic or quartz glass that can pass UV light, and can be clear or diffused. LGP 170 is an optical component and made of PMMA (acrylic) so as to pass all wavelengths of UV light and can be eliminated if using side-emitting UV LED emitters (not shown). Positive wire lead 160A and negative wire lead 160B connect to LED control electronics 100 to provide power to LED circuit board 140. LED circuit board 140 can be rigid or flexible. Optional LGP 170 sits inside the LED circuit board 140 with all UV LED emitters 150A, 150B, and 150C pointed at the edge of LGP 170 directing UV light into LGP 170. Special dot matrix print design on LGP 170 bends and mixes the UV light from UV LED emitters 150A, 150B, and 150C at right angles out onto particulate collector 180 to be viewed through opening 200 of front housing 190 by a user or observer. Besides the UV light being generated by individual UVA LED emitter 150A, UVB LED emitter 150B, and UVC LED emitter 150C, the present IPD device 10 invention can use a specially manufactured at least one multi-die UV LED emitter (not shown) consisting of at least one UVA LED emitter 150A, at least one UVB LED emitter 150B, and at least one UVC LED emitter 150C all in an at least one UV LED package.

Figure 2:
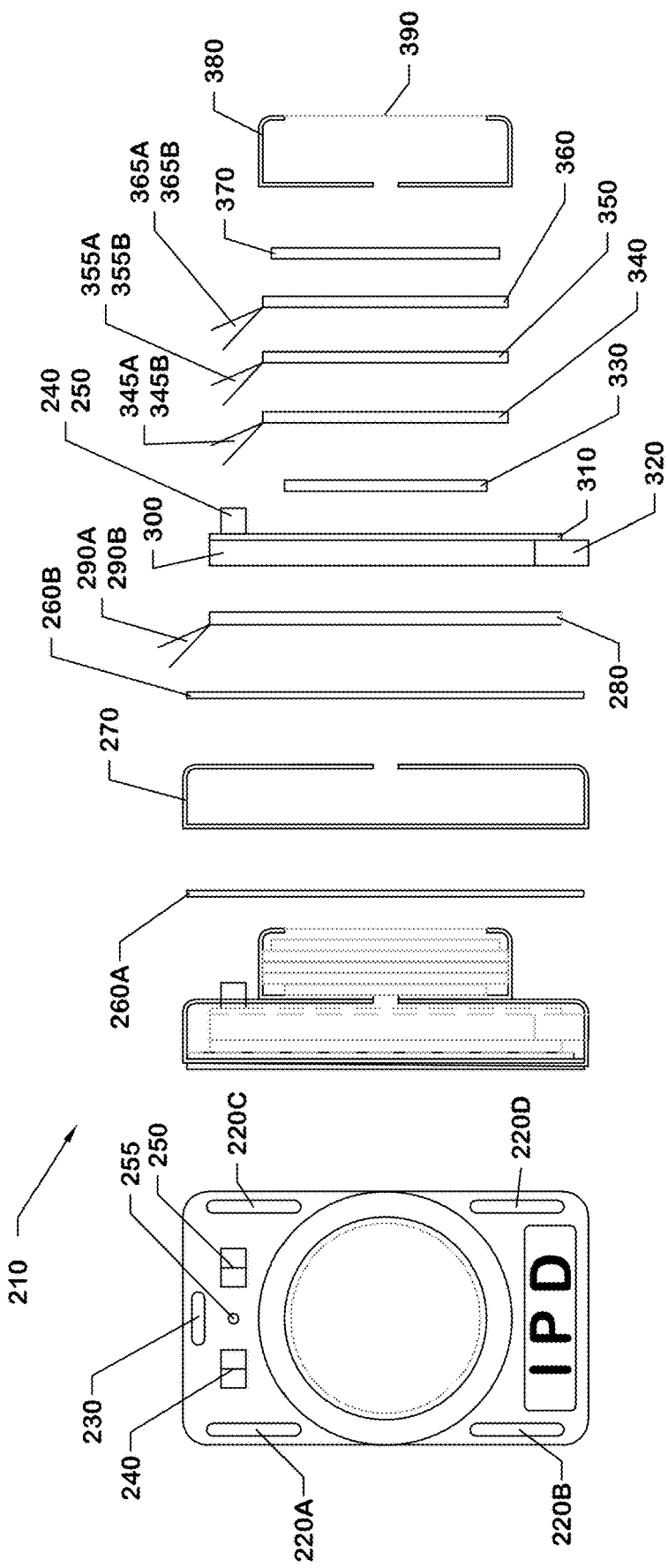
FIG. 2 shows a front and side views and assembly view of an alternate construction of the first embodiment of a multi-band UV light IPD device shown in FIG. 1 now using at least one electroluminescent UV OLED as the UV light source set within a housing including other components to be used as a standalone Instant Particulate Detector device.

FIG. 2 shows full front and side views and assembly view of an alternate construction of the first embodiment of a multi-band UV light Instant Particulate Detector (IPD) device 10 shown in FIG. 1. IPD device 210 now uses one EL UVA OLED 340, one EL UVB OLED 350, and one EL UVC OLED 360 as the primary UV light sources set within a front housing 380 including sharing the same back reflector substrate 330 in standalone Instant Particulate Detector device 210. Other configurations of EL UV OLEDs may include the use of one EL UVABC OLED (not shown) and one EL UVC OLED 360, or one EL UVAB OLED (not shown) and one EL UVC OLED 360. IPD device 210 includes passageway slots 220A, 220B, 220C, and 220D for straps (not shown), so that IPD device 210 can be worn on the upper arm of a user. A top passageway slot 230 is also provided for use with a lanyard or neck strap (not shown) if the user decides to wear the IPD device 210 around the neck. IPD device 210 can then be used like a name badge tag or hanging pendant. Both methods of hanging IPD device 210 will allow the user easy viewing of the front opening 390 of IPD device 210.

Power switch 240 allows IPD device 210 to be turned ON or OFF manually by a user, and mode select switch 250 allows the user to manually set the IPD device 210 in DETECTION mode or in DISINFECTION mode. In the preferred DETECTION mode setting, EL UVA OLED 340, EL UVB OLED 350, and EL UVC OLED 360 are all energized at the same time. In the alternate configuration of one EL UVABC OLED (not shown) and one EL UVC OLED 360, only EL UVABC OLED (not shown) is energized in the DETECTION mode. And in the last configuration of one EL UVAB OLED (not shown) and one EL UVC OLED 360, both EL UVAB OLED (not shown) and one EL UVC OLED 360 are both energized in the DETECTION mode setting. In the preferred DISINFECTION mode setting, only EL UVC OLED 360 is energized and both EL UVA OLED 340 and EL UVB OLED 350 remain off. In the alternate configuration of one EL UVABC OLED (not shown) and one EL UVC OLED 360, only EL UVC OLED 360 is energized in DISINFECTION mode and EL UVABC OLED (not shown) remains off. And in the last configuration of one EL UVAB OLED (not shown) and one EL UVC OLED 360, only EL UVC OLED 360 is energized in the DISINFECTION mode setting and EL UVAB OLED (not shown) remains off. Speaker hole 255 is optional and is triggered by a small light sensor (not shown) to provide an additional audio alarm alert to supplement the visual instant detection front opening 390 of the IPD device 210. Lastly, there is a section marked "IPD" that can be used to display any logo to help identify IPD device 210.

Moving on to the next component in IPD device 210 is a thin double-sided adhesive strip 260A serving as yet another method for attaching IPD device 210 to a smooth flat surface to temporarily mount the IPD device 210 to a wall or smooth flat surface (not shown). In some instances, thin double-sided adhesive strip 260A can be a thin steel metal plate with one-sided adhesive for attaching the thin steel metal back plate to the back of rear housing 270 of IPD device 210. This will allow IPD device 210 to be used with commercially available magnetic mounts (not shown) for holding IPD device 210 in place as a stationary instant particulate detector IPD device 210 for use in a room or vehicle, etc.

Rear housing 270 of IPD device 210 is preferably made of lightweight and durable plastic. Rear housing 270 contains thin double-sided adhesive strip 260B, battery 280, and LED control electronics 300 and printed circuit board 310. Battery 280 is a thin and low profile Lithium-Ion type rechargeable battery like LiPo or Lithium-Ion Polymer with a positive lead 290A and a negative lead 290B that connects to LED control electronics 300 and printed circuit board 310. Switches 240 and 250 are connected to and are part of LED control electronics 300 and printed circuit board 310. USB charging port 320 is provided and is also part of the LED control electronics 300 and printed circuit board 310 to charge battery 280. LED control electronics 300 also contains an IC controller and driver (not shown) that supplies power to EL UV OLEDs 340, 350, and 360 with preferably a constant voltage. When a charging cable (not shown) is connected to USB charging port 320, the IPD device 210 is powered by the USB charger (not shown) that also charges battery 280. When the IPD device 210 is removed from the USB charger (not shown), battery 280 powers the IPD device 210.

Front housing 380 of IPD device 210 is also preferably made of lightweight and durable plastic and attaches to rear housing 270 by attachment means (not shown). Front housing 380 contains shared back reflector substrate 330, one EL UVA OLED 340 with positive wire lead 345A and negative wire lead 345B, one EL UVB OLED 350 with positive wire lead 355A and negative wire lead 355B, one EL UVC OLED 360 with positive wire lead 365A and negative wire lead 365B, and particulate collector 370. Back reflector substrate 330 is shared and located behind EL UV OLEDs 340, 350, and 360. It uses a reflective surface material and preferably has a dark or black background color to reflect any stray UV light outward, so as to reduce glare and will only fluoresce and glow particulates collected on particulate collector 370. Particulate collector 370 can be made of PMMA acrylic or quartz glass that can pass UV light, and can be clear or diffused. Positive wire leads 345A, 355A, and 365A and negative wire leads 345B, 355B, and 365B all connect to LED control electronics 300 to provide power to EL UV OLEDs 340, 350, and 360 emitting UV light out onto particulate collector 370 through opening 390 of front housing 380 to be viewed by a user or observer.

Figure 3:
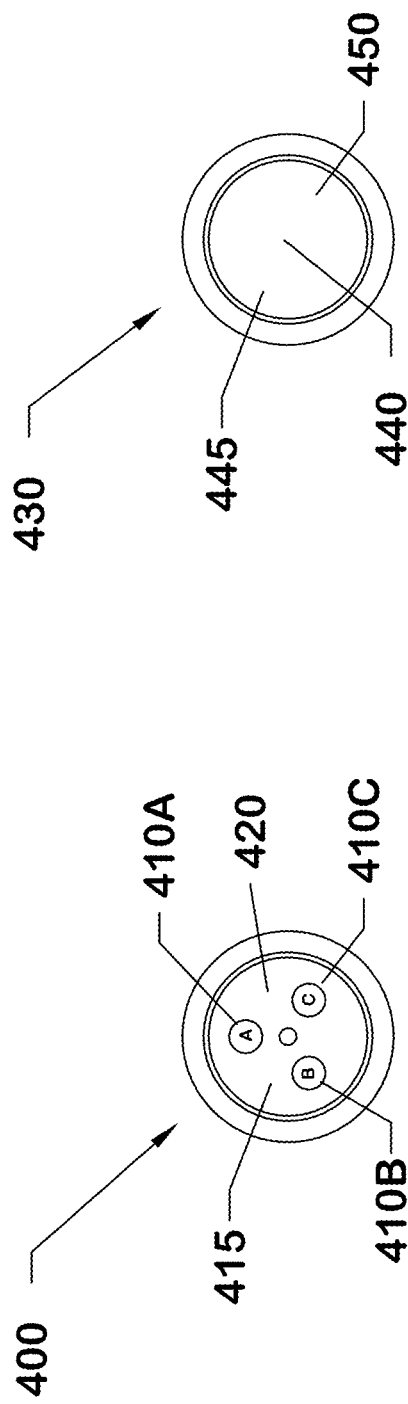
FIG. 3A shows a front view of a battery replaceable round IPD dot device as described in FIG. 1 of the present invention.
FIG. 3B shows a front view of a battery replaceable round IPD dot device as described in FIG. 2 of the present invention.

FIG. 3A shows a front view of a battery replaceable round Instant Particulate Detector IPD device 400 as described in FIG. 1 of the present invention. IPD device 400 is a simplified embodiment of the present invention of FIG. 1. It is now a lower cost IPD device 400 made in the shape of a circular dot. It incorporates one UVA LED emitter 410A, one UVB LED emitter 410B, and one UVC LED emitter 410C set against background reflector 415 for detection purposes of any droplet particulates that may be collected and fluoresces on particulate collector 420. Instead of separate UV LED emitters 410A, 410B, 410C, a single multi-die UV LED (not shown) incorporating one each of a UVA LED emitter 410A, a UVB LED emitter 410B, and a UVC LED emitter 410C may be developed and used as the main UV light source in IPD device 400. An optional multi-position push button switch (not shown) may be incorporated into compact circular dot IPD device 400 for power and to select the different modes of operation. Optional disinfection is done using UVC emitter 410C only, and uses low cost replaceable button type batteries (not shown). Velcro strips or very high bond double sided tape (not shown) can be used to mount compact circular dot IPD device 400 to protective gear (not shown).

FIG. 3B shows a front view of a battery replaceable round Instant Particulate Detector IPD device 430 as described in FIG. 2 of the present invention. IPD device 430 is a simplified embodiment of the present invention of FIG. 2. It is now a lowest cost IPD device 430 made in the shape of a circular dot. It incorporates one EL UVABC OLED 440 set against background reflector substrate 445 for detection purposes only of droplet particulates that may be collected and fluoresces on particulate collector 450. No switches or disinfection is available to reduce cost for the part in mass production. Velcro strips or very high bond double sided tape (not shown) can be used to mount compact circular dot IPD device 430 to protective gear (not shown).

Figure 4:
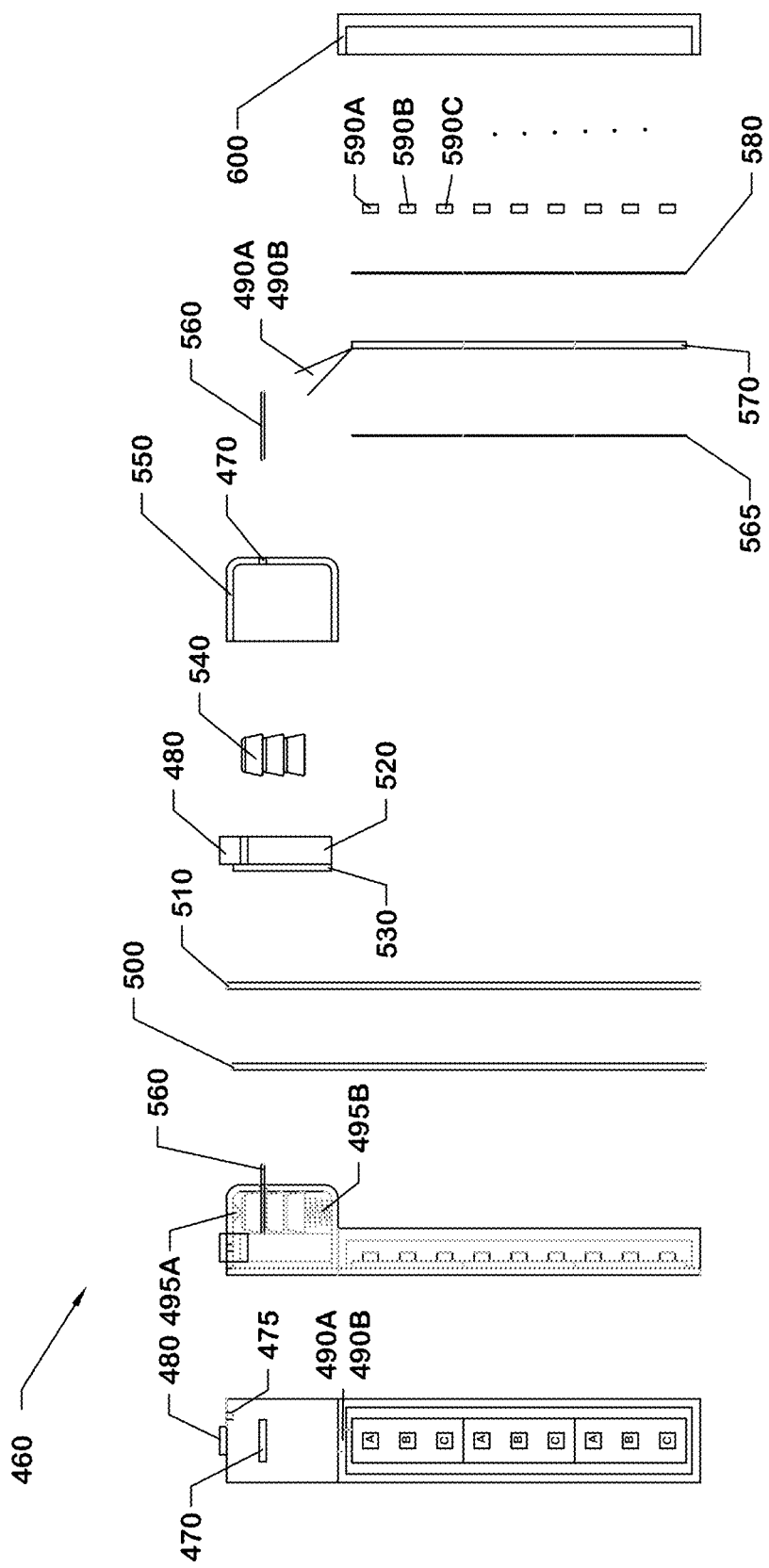
FIG. 4 shows a front and side views and assembly view of a second embodiment of a flexible multi-band UV light device using at least one each of a UVA, UVB, and UVC LED emitters as the UV light source arranged in a linear array including other components to be used with Personal Protective Equipment.

FIG. 4 shows full front and side views and assembly view of a second embodiment of a multi-band UV light Instant Particulate Detector (IPD) device 460 using at least one each of a UVA LED emitter 590A, UVB LED emitter 590B, and UVC LED emitter 590C as the main UV light sources arranged in a linear array under particulate collector 600 including other components provided on bottom housing plate 510 in an Instant Particulate Detector IPD device 460 that can be used with Personal Protective Equipment (not shown). IPD device 460 will allow the user to easily view the particulate collector 600 of IPD device 460.

Combination switch 480 allows IPD device 460 to be turned ON and OFF manually by a user, and allows the user to manually set the IPD device 460 in either DETECTION mode or in DISINFECTION mode. In the DETECTION mode setting, at least one UVA LED emitter 590A, at least one UVB LED emitter 590B, and at least one UVC LED emitter 590C are all energized at the same time. In the DISINFECTION mode setting, at least one UVC LED emitter 590C is energized only. The at least one UVA LED emitter 590A and at least one UVB LED emitter 590B remain off. Speaker hole 475 is optional and is triggered by a small light sensor (not shown) to provide an additional audio alarm alert to supplement the visual instant detection on particulate collector 600 of the IPD device 460. Next in IPD device 460 is a thin double-sided adhesive strip 500 serving as the method for attaching IPD device 460 to a smooth flat surface and to temporarily mount the IPD device 40 to personal protective equipment (not shown).

Bottom housing plate 510 and top housing 550 of IPD device 460 is preferably made of lightweight and durable plastic. Top housing 550 contains replaceable batteries 540, and LED control electronics 520 and printed circuit board 530. Batteries 540 are small replaceable button types similar to LR44 batteries and others (not shown) that connect to a positive contact 495A and to a negative contact 495B that communicates with LED control electronics 520 and printed circuit board 530. Switch 480 is connected to and is part of LED control electronics 520 and printed circuit board 530. LED control electronics 520 also contains an IC controller and driver (not shown) that supplies power to UV LED emitters 590A, 590B, and 590C preferably with a constant voltage. Slot 470 is provided on top housing 550 to for a non-conductive plastic barrier strip 560 to be manually inserted into slot 470, so as to disconnect batteries 540 from LED control electronics 520 and prevent accidental waste of power during shipping and transportation of IPD device 460. During normal operation, the plastic barrier strip 560 is removed and replaceable batteries 540 provide power to the IPD device 460.

Bottom housing plate 510 of IPD device 460 attaches to top housing 550 by attachment means (not shown). Bottom housing plate 510 further contains thermal adhesive pad 565, LED circuit board 570 with positive wire lead 490A and negative wire lead 490B, outer layer background reflector 580, at least one UVA LED emitter 590A, at least one UVB LED emitter 590B, at least one UVC LED emitter 590C, and particulate collector 600. Outer layer background reflector 580 is located between LED circuit board 570 and UV LED emitters 590A, 590B, and 590C. It uses a reflective surface material and preferably has a dark or black background color, so as to reduce glare and will only fluoresce and glow particulates collected on particulate collector 600. Particulate collector 600 can be made of silicone or PMMA acrylic that can pass UV light, and can be clear or diffused. Positive wire lead 490A and negative wire lead 490B connect to LED control electronics 520 to provide power to LED circuit board 570. LED circuit board 570 can be rigid or flexible. LED circuit board 570 in combination with outer layer background reflector 580 and all UV LED emitters 590A, 590B, and 590C direct UV light out onto particulate collector 600 to be viewed by a user or observer. Besides the UV light being generated by individual UVA LED emitter 590A, UVB LED emitter 590B, and UVC LED emitter 590C, the present IPD device 460 invention can use a specially manufactured at least one multi-die UV LED emitter (not shown) consisting of at least one UVA LED emitter 590A, at least one UVB LED emitter 590B, and at least one UVC LED emitter 590C all in an at least one UV LED package.

Figure 5:
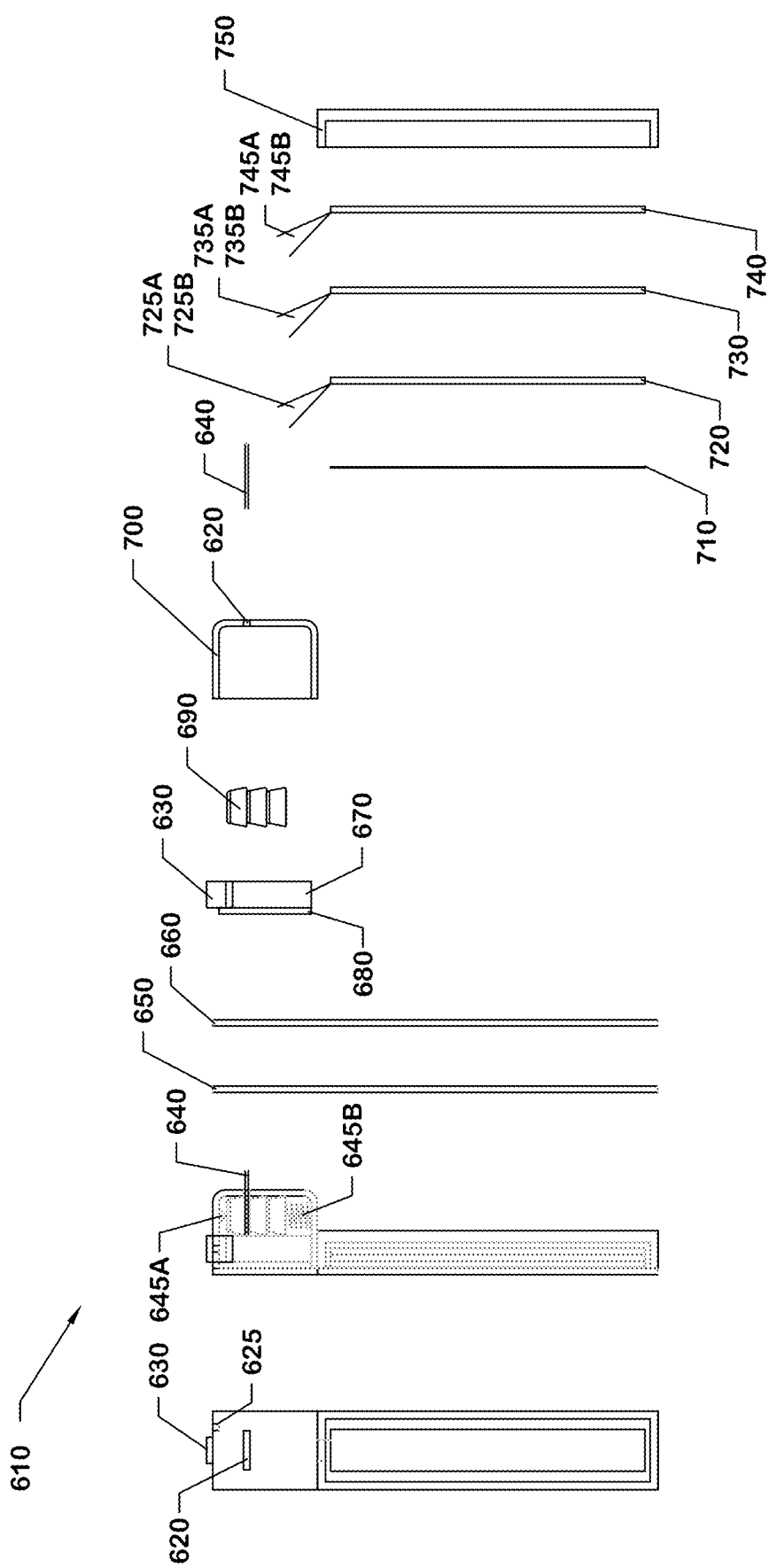
FIG. 5 shows a front and side views and assembly view of an alternate construction of the second embodiment of a multi-bank UV LED IPD device shown in FIG. 4 now using at least one electroluminescent UV OLED as the UV light source including other components to be used with Personal Protective Equipment.

FIG. 5 shows full front and side views and assembly view of an alternate construction of the second embodiment of a multi-band UV light Instant Particulate Detector (IPD) device 460 shown in FIG. 4. IPD device 610 now uses one EL UVA OLED 720, one EL UVB OLED 730, and one EL UVC OLED 740 as the primary UV light sources stacked on top of bottom housing plate 660 including sharing the same back reflector substrate 710 in Instant Particulate Detector IPD device 610 that can be used with Personal Protective Equipment (not shown). Other configurations of EL UV OLEDs may include the use of one EL UVABC OLED (not shown) and one EL UVC OLED 740, or one EL UVAB OLED (not shown) and one EL UVC OLED 740. IPD device 610 will allow the user to easily view the particulate collector 750 of IPD device 610.

Combination switch 630 allows IPD device 610 to be turned ON and OFF manually by a user, and allows the user to manually set IPD device 610 in either DETECTION mode or in DISINFECTION mode. In the preferred DETECTION mode setting, EL UVA OLED 720, EL UVB OLED 730, and EL UVC OLED 740 are all energized at the same time. In the alternate configuration of one EL UVABC OLED (not shown) and one EL UVC OLED 740, only EL UVABC OLED (not shown) is energized in the DETECTION mode. And in the last configuration of one EL UVAB OLED (not shown) and one EL UVC OLED 740, both EL UVAB OLED (not shown) and one EL UVC OLED 740 are both energized in the DETECTION mode setting. In the preferred DISINFECTION mode setting, only EL UVC OLED 740 is energized and both EL UVA OLED 720 and EL UVB OLED 7300 remain off. In the alternate configuration of one EL UVABC OLED (not shown) and one EL UVC OLED 740, only EL UVC OLED 740 is energized in DISINFECTION mode and EL UVABC OLED (not shown) remains off. And in the last configuration of one EL UVAB OLED (not shown) and one EL UVC OLED 740, only EL UVC OLED 360 is energized in the DISINFECTION mode setting and EL UVAB OLED (not shown) remains off. Speaker hole 625 is optional and is triggered by a small light sensor (not shown) to provide an additional audio alarm alert to supplement the visual instant detection on particulate collector 750 of the IPD device 610. Next in IPD device 610 is a thin Velcro or very high bond double-sided adhesive strip 650 serving as the method for attaching IPD device 610 to a smooth flat surface and to temporarily mount the IPD device 610 to personal protective equipment (not shown).

Bottom housing plate 660 and top housing 700 of IPD device 610 is preferably made of lightweight and durable plastic. Top housing 700 contains replaceable batteries 690, and LED control electronics 670 and printed circuit board 680. Batteries 690 are small replaceable button types similar to LR44 batteries and others (not shown) that connect to a positive contact 645A and to a negative contact 645B that communicates with LED control electronics 670 and printed circuit board 680. Switch 630 is connected to and is part of LED control electronics 670 and printed circuit board 680. LED control electronics 670 also contains an IC controller and driver (not shown) that supplies power to EL UV OLEDs 720, 730, and 740 with preferably a constant voltage. Slot 620 is provided on top housing 700 for a non-conductive plastic barrier strip 640 to be manually inserted into slot 620 so as to disconnect batteries 690 from LED control electronics 670 and prevent accidental waste of power during shipping and transportation of IPD device 610. During normal operation, the plastic barrier strip 640 is removed and replaceable batteries 690 provide power to the IPD device 610.

Bottom housing plate 660 of IPD device 610 attaches to top housing 700 by attachment means (not shown). Bottom housing plate 660 further contains optional thermal adhesive pad (not shown), shared back reflector substrate 710, one EL UVA OLED 720 with positive wire lead 725A and negative wire lead 725B, one EL UVB OLED 730 with positive wire lead 735A and negative wire lead 735B, one EL UVC OLED 740 with positive wire lead 745A and negative wire lead 745B, and particulate collector 750. Back reflector substrate 710 is shared and located behind EL UV OLEDs 720, 730, and 740. It uses a reflective surface material and preferably has a dark or black background color to reflect any stray UV light outward, so as to reduce glare and will only fluoresce and glow particles collected on particulate collector 750. Particulate collector 750 can be made of silicone or PMMA acrylic that can pass UV light, and can be clear or diffused. Positive wire leads 725A, 735A, and 745A and negative wire leads 725B, 735B, and 745B all connect to LED control electronics 670 to provide power to EL UV OLEDs 720, 730, and 740 emitting UV light out onto particulate collector 750 to be viewed by a user or observer.

Figure 6:
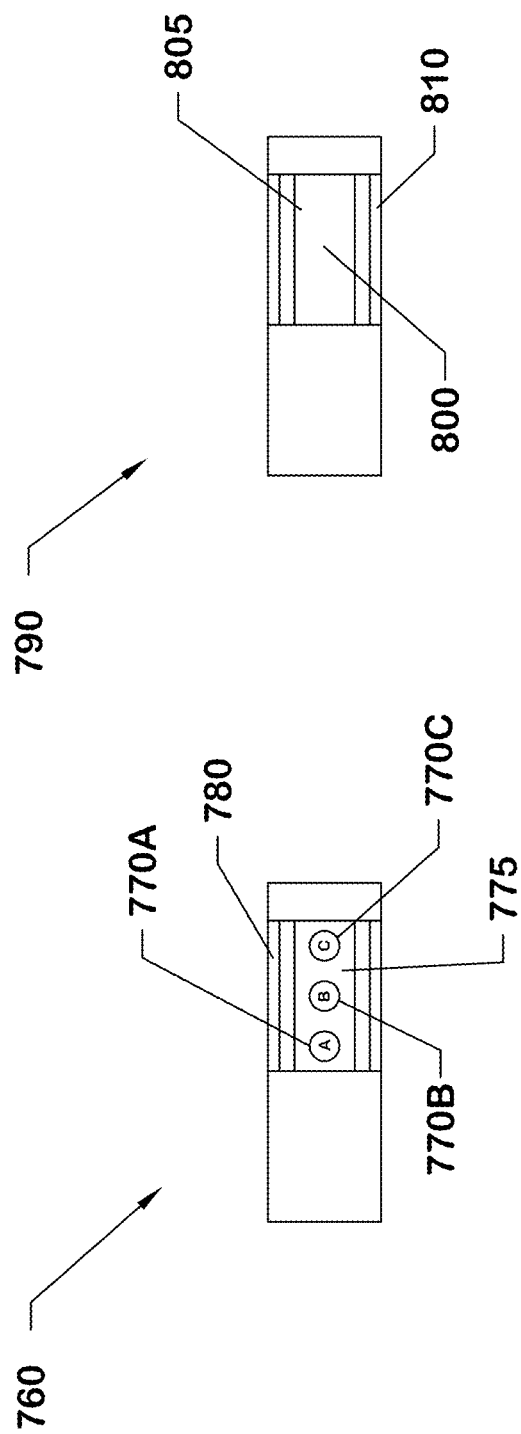
FIG. 6A shows a front view of a battery replaceable linear rectangular strip IPD device as described in FIG. 4 of the present invention.
FIG. 6B shows a front view of a battery replaceable linear rectangular strip IPD device as described in FIG. 5 of the present invention.

FIG. 6A shows a front view of a battery replaceable linear rectangular strip Instant Particulate Detector IPD device 760 as described in FIG. 4 of the present invention. IPD device 760 is a simplified embodiment of the present invention of FIG. 4. It is now a lower cost IPD device 760 made in the shape of a compact linear rectangular strip. It incorporates one UVA LED emitter 770A, one UVB LED emitter 770B, and one UVC LED emitter 770C set against background reflector 775 for detection purposes of any droplet particulates that may be collected and fluoresces on particulate collector 780. Instead of separate UV LED emitters 770A, 770B, 770C, a single multi-die UV LED (not shown) incorporating one each of a UVA LED emitter 770A, a UVB LED emitter 770B, and a UVC LED emitter 770C may be developed and used as the main UV light source in IPD device 760. An optional multi-position push button switch (not shown) may be incorporated into compact linear rectangular strip IPD device 760 for power and to select the different modes of operation. Optional disinfection is done using UVC emitter 770C only, and uses low cost replaceable button type batteries (not shown). Velcro strips or very high bond double sided tape (not shown) can be used to mount compact linear rectangular strip IPD device 760 to protective gear (not shown).

FIG. 6B shows a front view of a battery replaceable linear rectangular strip Instant Particulate Detector IPD device 790 as described in FIG. 5 of the present invention. IPD device 790 is a simplified embodiment of the present invention of FIG. 5. It is now a lowest cost IPD device 790 made in the shape of a compact linear rectangular strip. It incorporates one EL UVABC OLED 800 set against background reflector substrate 805 for detection purposes only of droplet particulates that may be collected and fluoresces on particulate collector 810. No switches or disinfection is available to reduce cost for the part in mass production. Velcro strips or very high bond double sided tape (not shown) can be used to mount compact linear rectangular strip IPD device 790 to protective gear (not shown).

Figure 7:
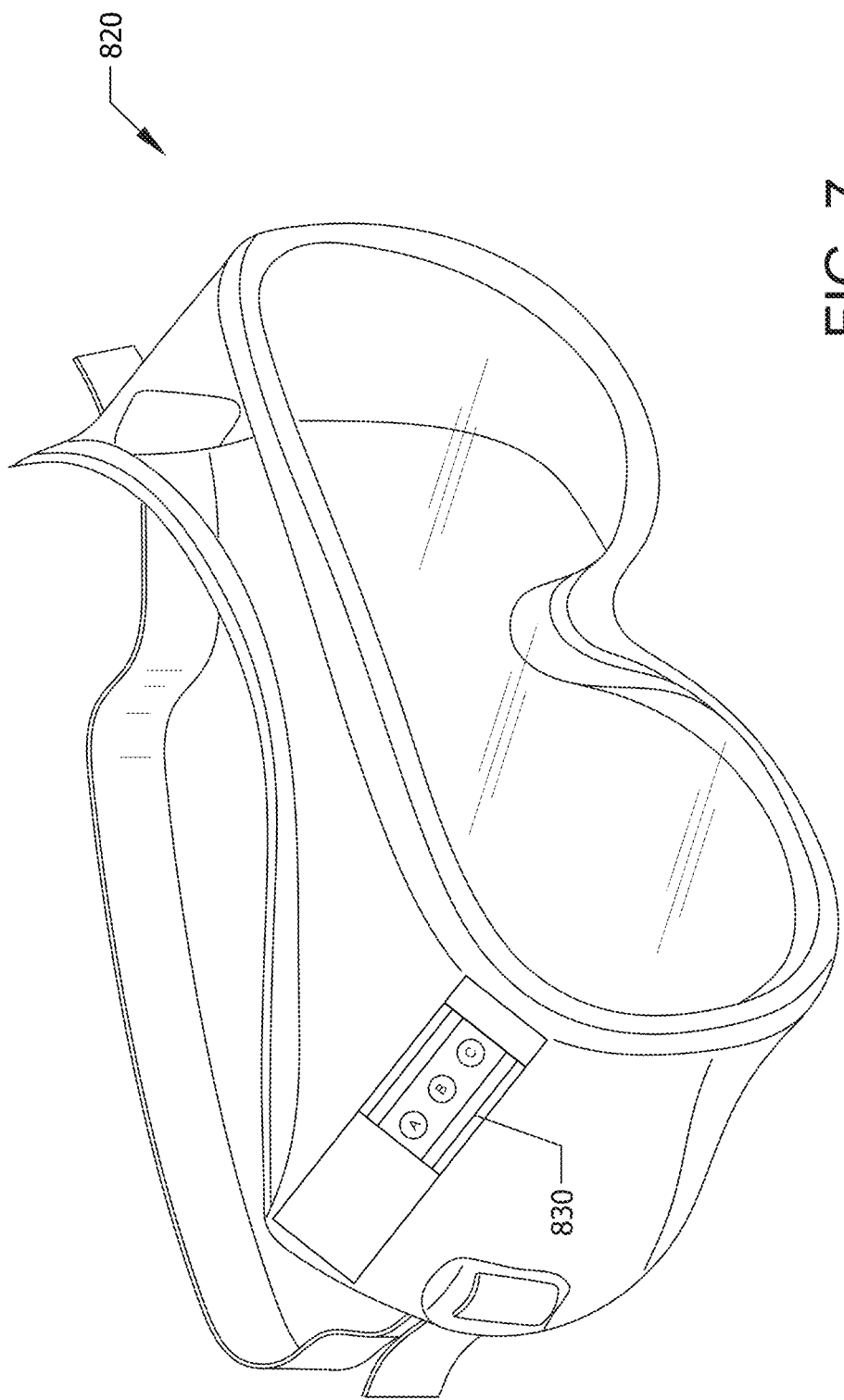
FIG. 7 shows the IPD device of FIG. 6A attached to a PPE safety goggle.

FIG. 7 shows IPD device 830 of FIG. 6A attached to PPE safety goggle 820.

Figure 8:
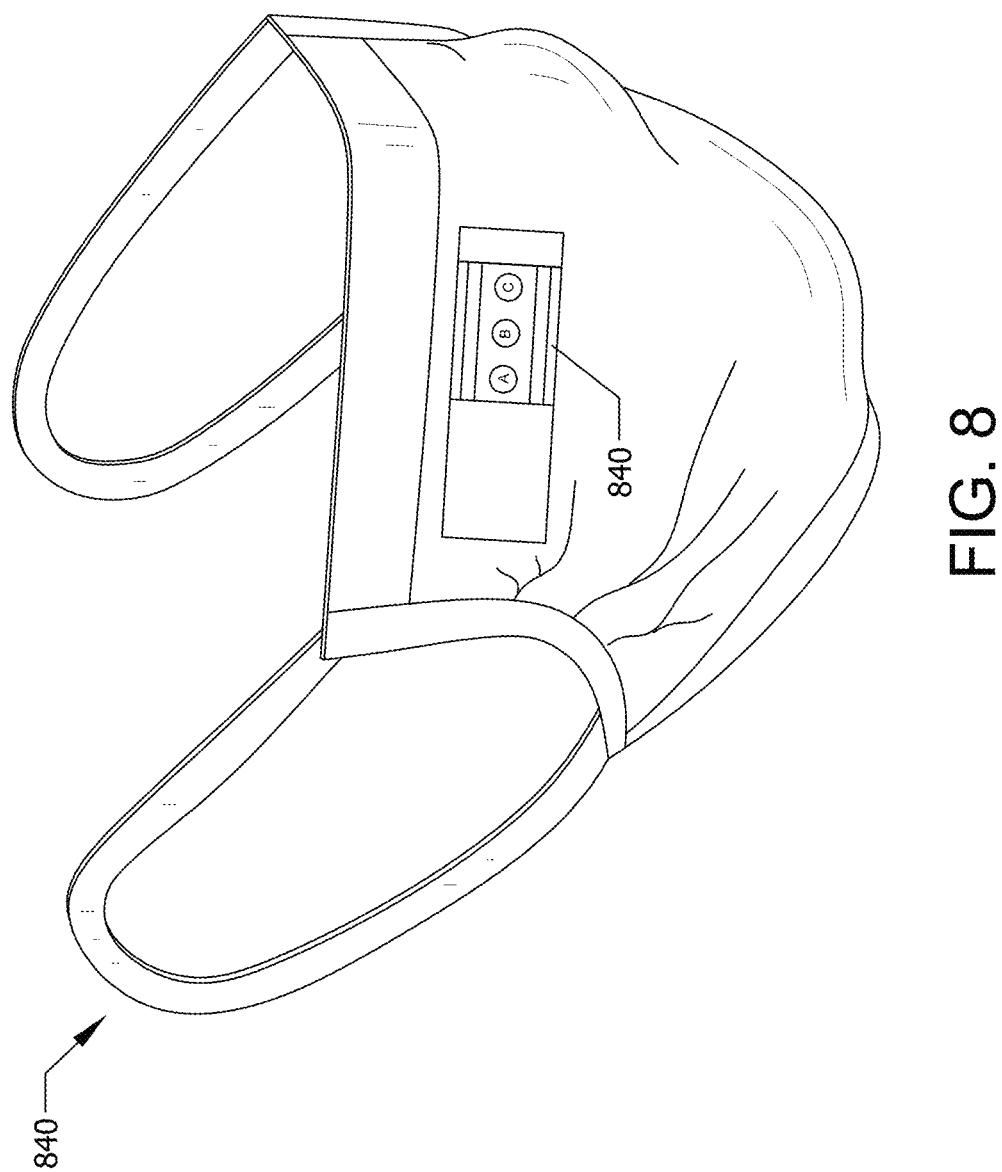
FIG. 8 shows the IPD device of FIG. 6A attached to a PPE face mask.

FIG. 8 shows IPD device 850 of FIG. 6A attached to PPE face mask 840.

Figure 9:
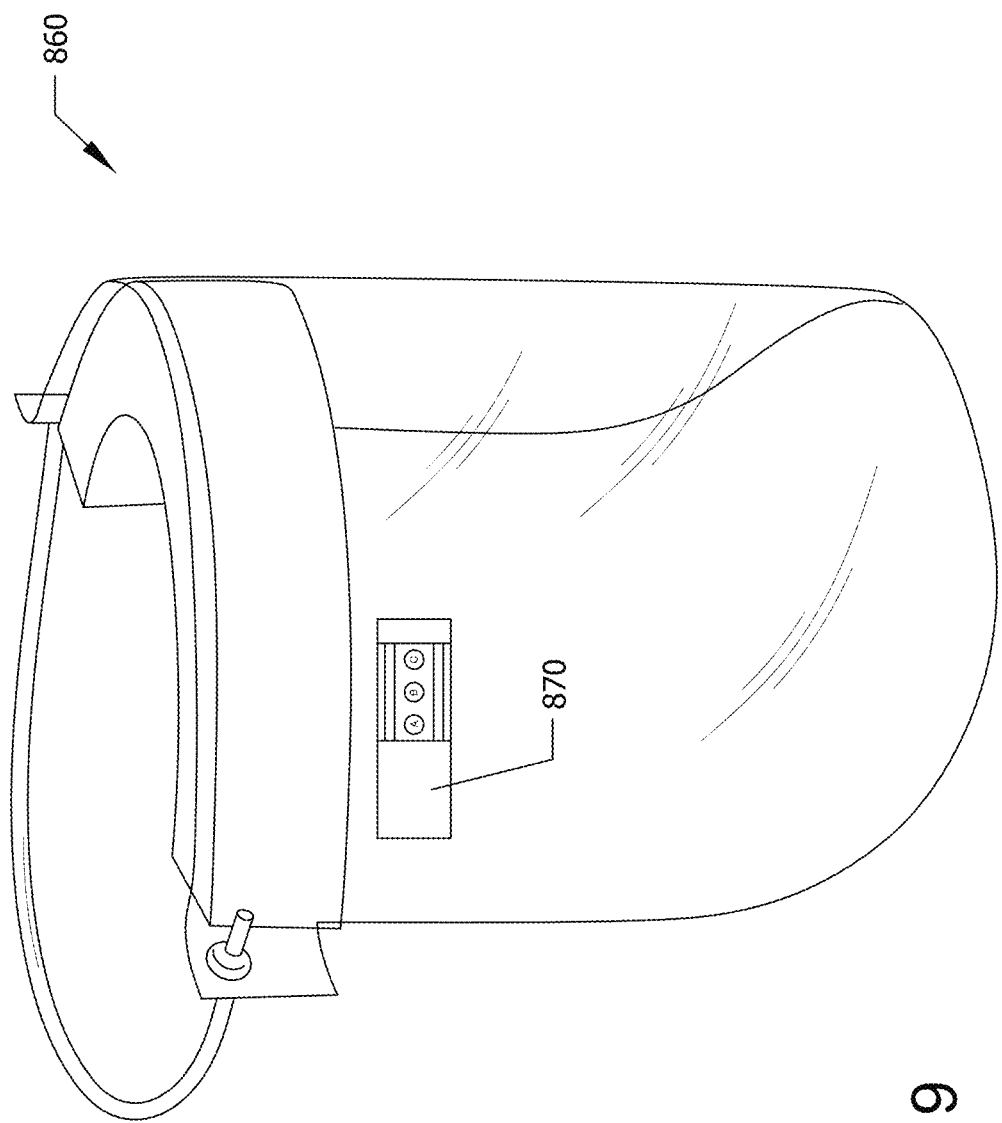
FIG. 9 shows the IPD device of FIG. 6A attached to a PPE face shield.

FIG. 9 shows IPD device 870 of FIG. 6A attached to PPE face shield 860.

Figure 10:
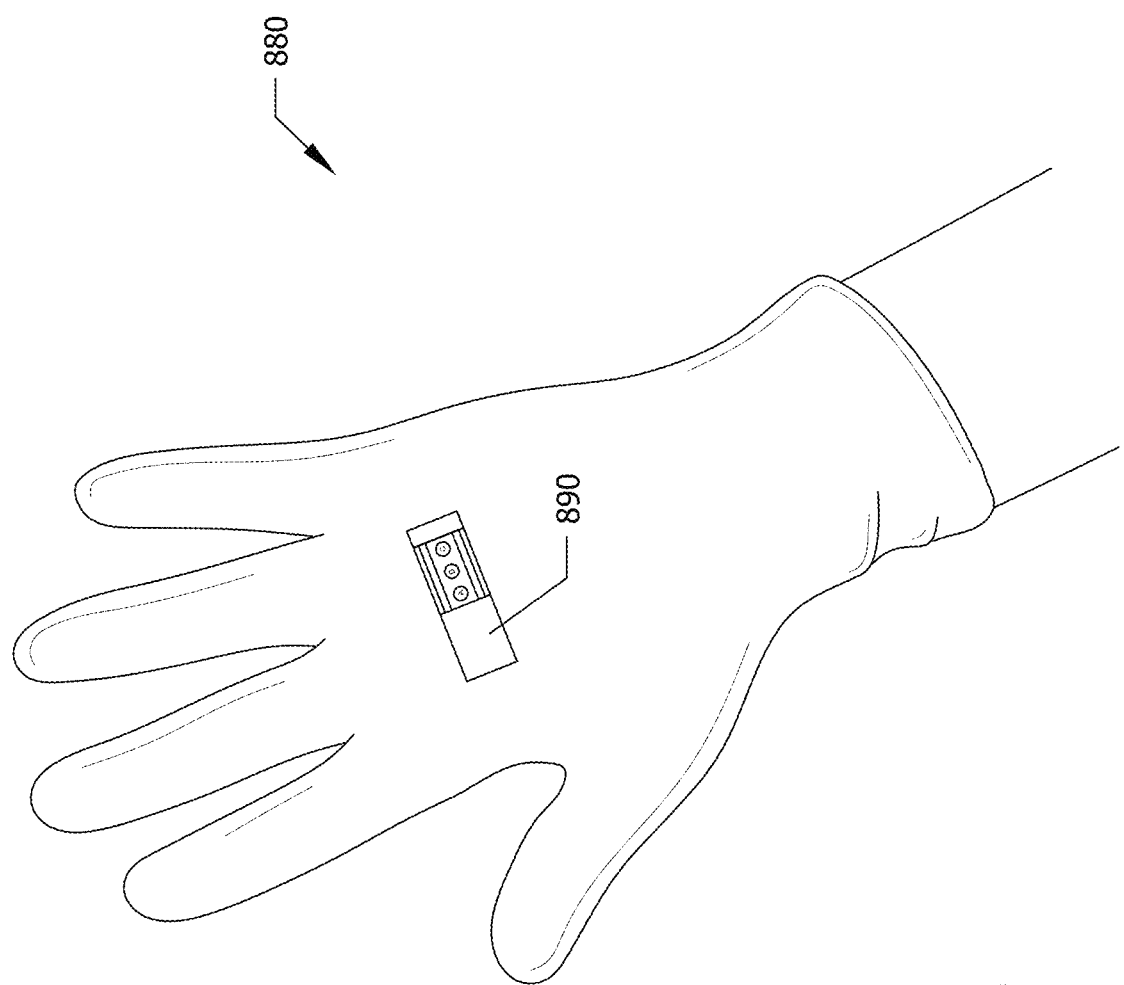
FIG. 10 shows the IPD device of FIG. 6A attached to a PPE safety glove.

FIG. 10 shows IPD device 890 of FIG. 6A attached to PPE safety glove 880.

Figure 11:
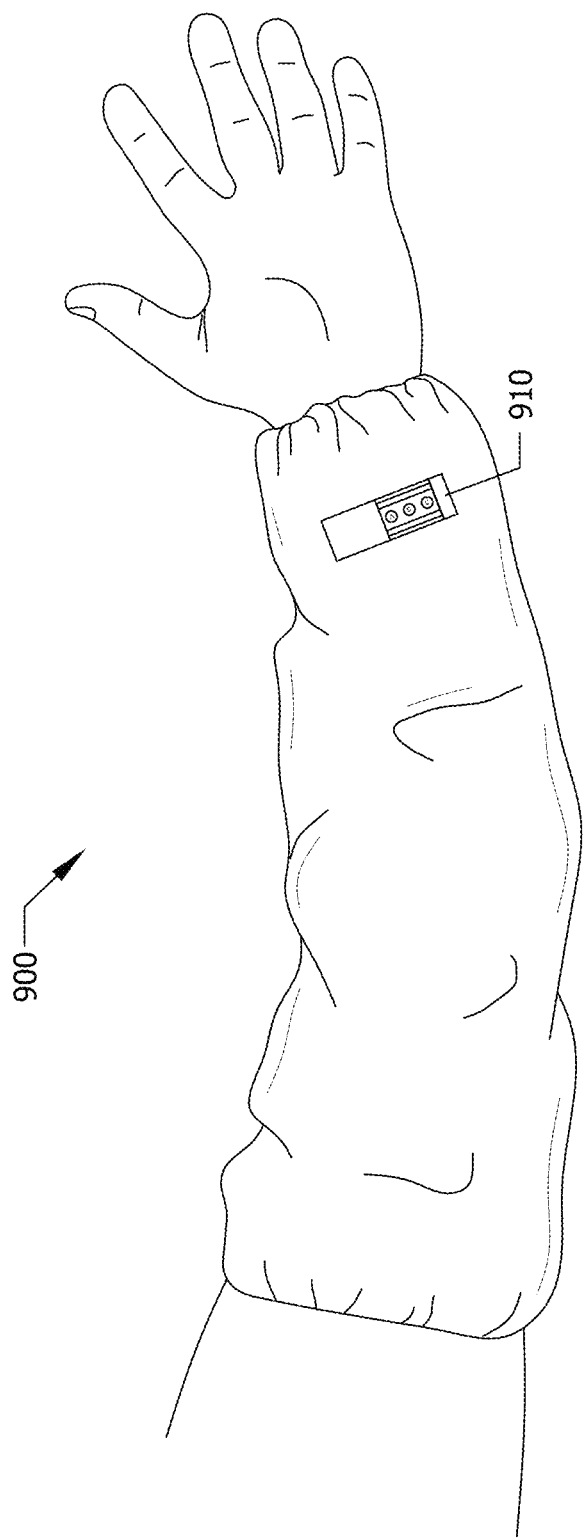
FIG. 11 shows the IPD device of FIG. 6A attached to a PPE arm sleeve.

FIG. 11 shows IPD device 910 FIG. 6A attached to PPE arm sleeve 900.

Figure 12:
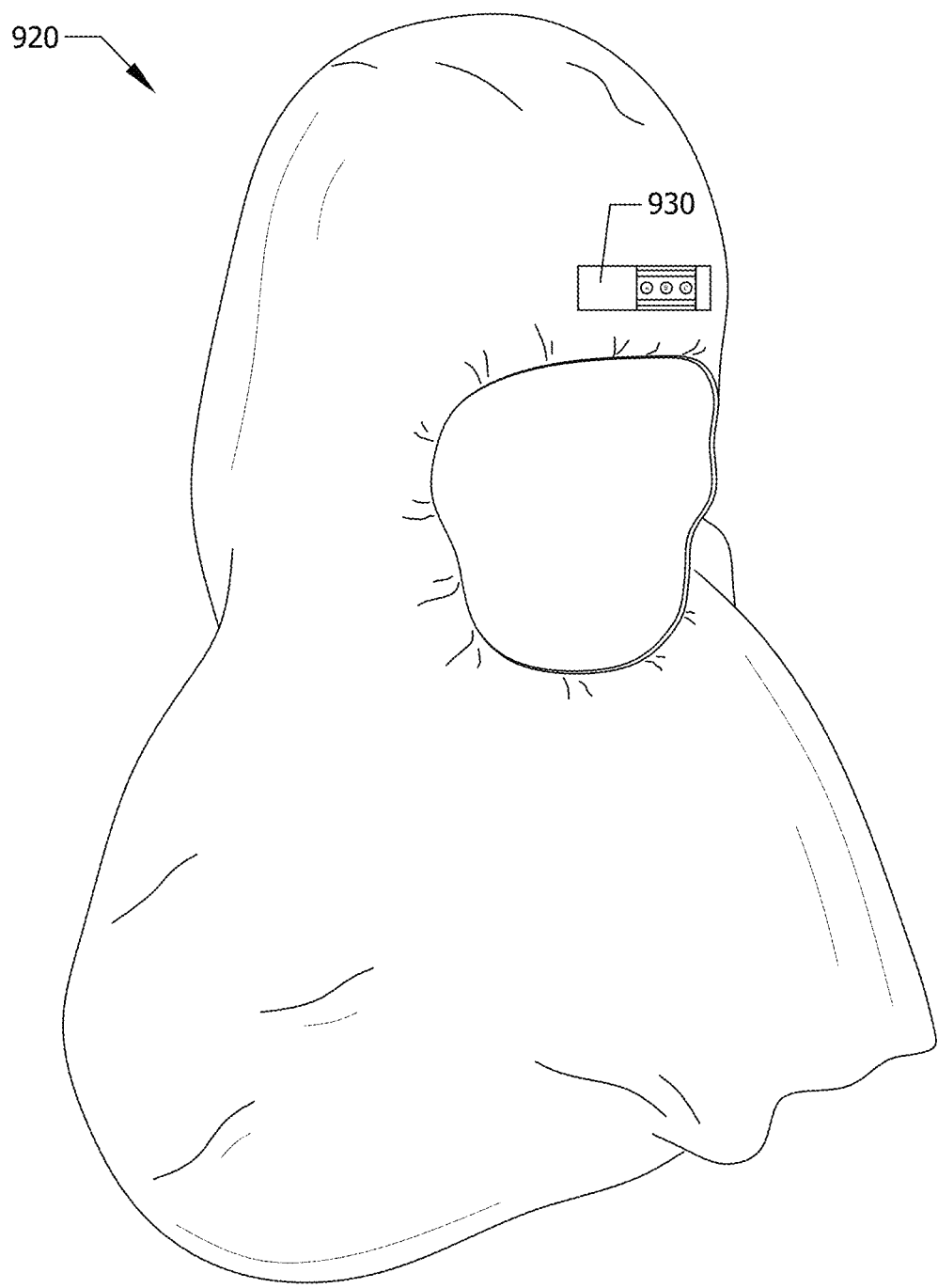
FIG. 12 shows the IPD device of FIG. 6A attached to a PPE head hood.

FIG. 12 shows IPD device 930 FIG. 6A attached to PPE head hood 920.

Figure 13:
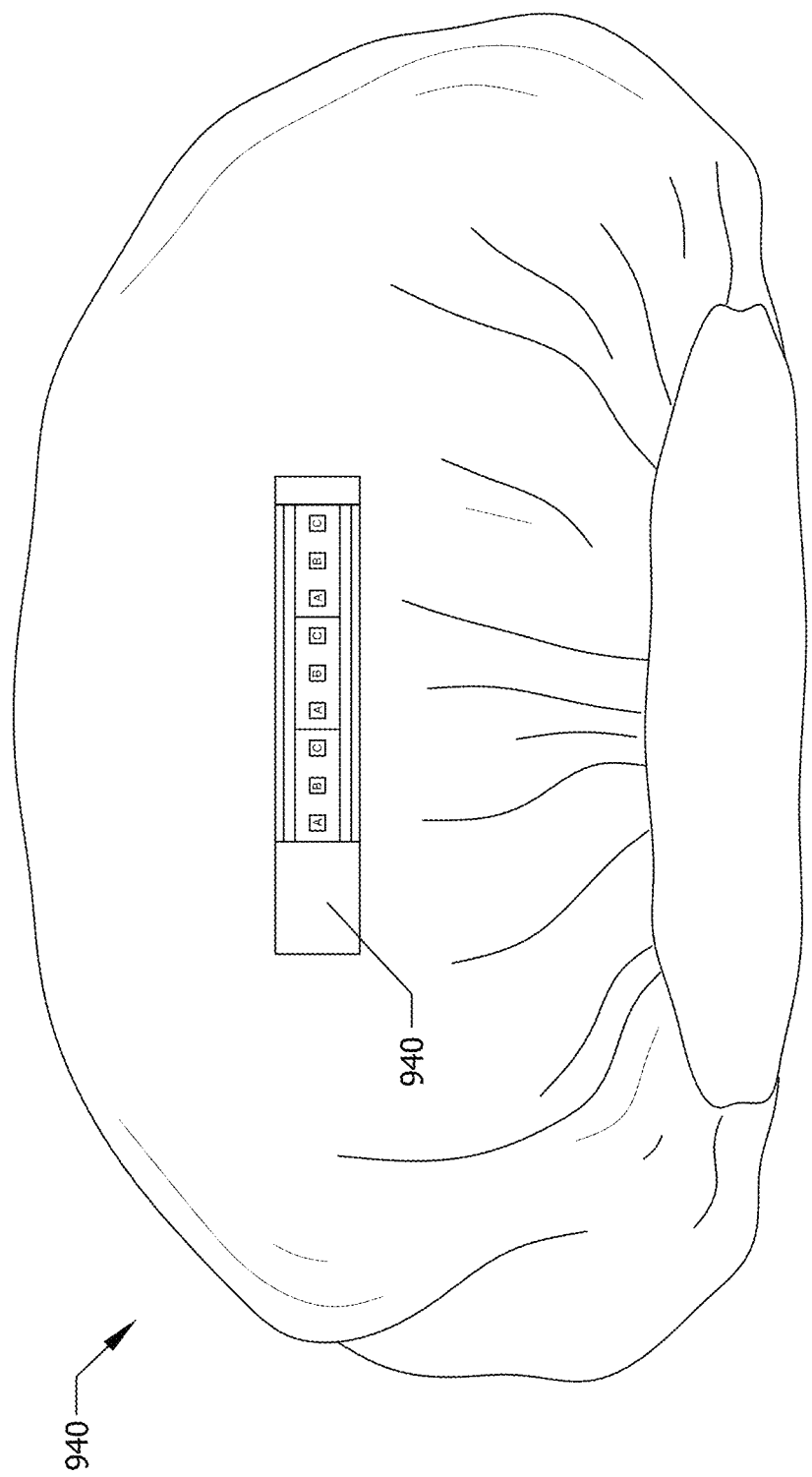
FIG. 13 shows the IPD device of FIG. 4 attached to a PPE solid hairnet.

FIG. 13 shows IPD device 950 FIG. 4 attached to PPE solid hairnet 940.

Figure 14:
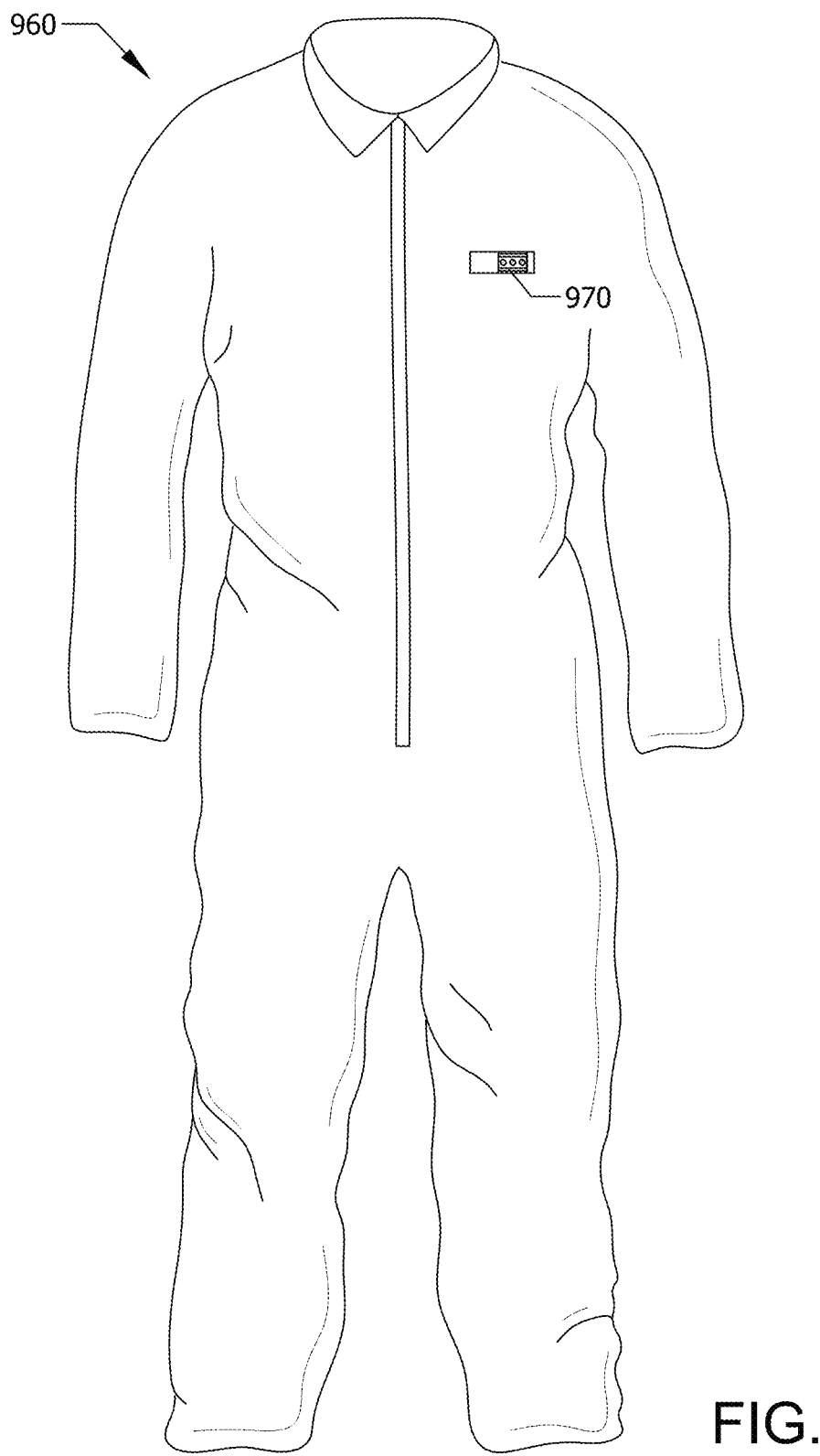
FIG. 14 shows the IPD device of FIG. 6A attached to a PPE body coverall.

FIG. 14 shows IPD device 970 FIG. 6A attached to PPE body coverall 960.

Figure 15:
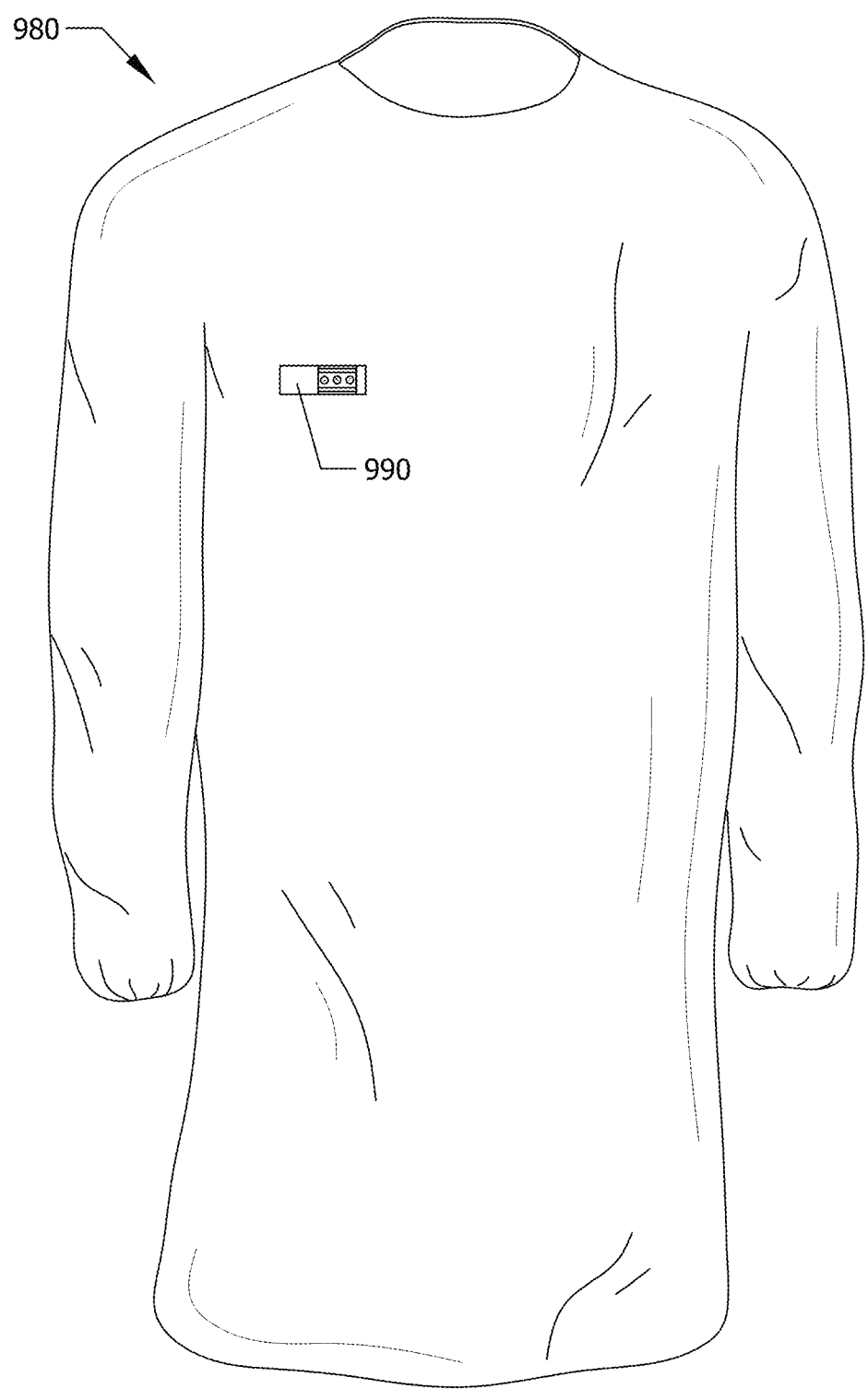
FIG. 15 shows the IPD device of FIG. 6A attached to a PPE body gown.

FIG. 15 shows IPD device 990 FIG. 6A attached to PPE body gown 980.

Figure 16:
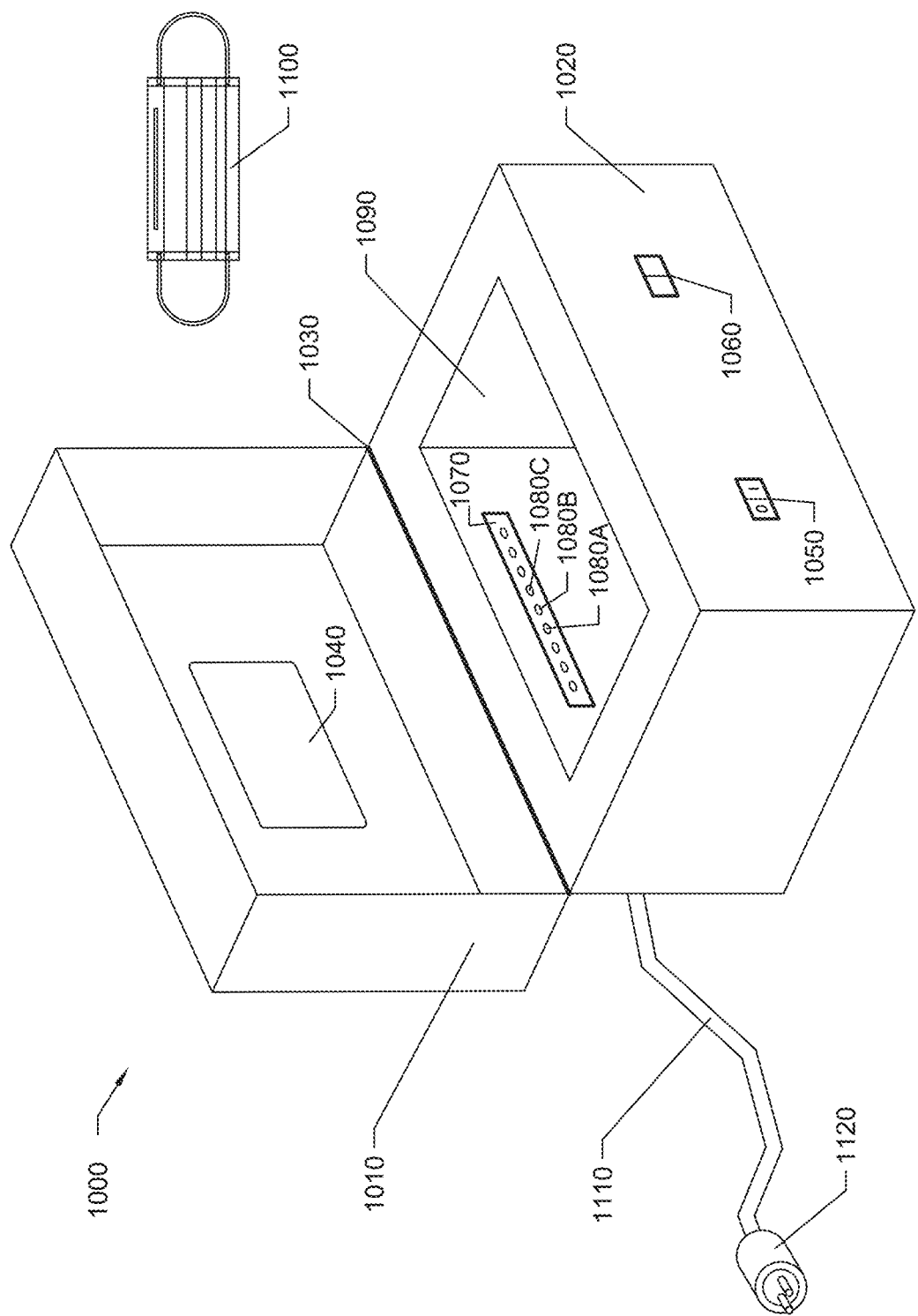
FIG. 16 shows an isometric view of a third embodiment of a multi-band UV light IPD device using at least one each of a UVA, UVB, and UVC LED emitters as the main source of UV light installed inside a box for the detection and subsequent disinfection of particulate collector PPE items that may have come in contact with harmful aerosol droplet particles.

FIG. 16 shows an isometric view of a third embodiment of a multi-band UV light based IPD device 1000 using at least one each of a UVA LED emitter 1080A, UVB LED emitter 1080B, and UVC LED emitter 1080C as the main source of UV light mounted to LED circuit board 1070, LED controller and optional battery (not shown) are all installed inside a deep bottom box 1020 with a hinge 1030 and top box lid cover 1010, and having an optional power supply cord 1110 and plug 1120 for continuous charging and operation of IPD device 1000. A viewing window 1040 on top box lid cover 1010 is provided for viewing the detection against dark background reflector 1090, and subsequent disinfection of particulate collector PPE like face mask 1100 that may have come in contact with harmful aerosol droplet particles (not shown). Other Personal Protective Equipment or PPE gear (not shown) and other objects including bags, mail, shoes, keys, etc. (not shown) may serve as particulate collectors as well for use in IPD device 1000. Switch 1050 is for ON or OFF, and switch 1060 selects the different modes of IPD device 1000. Besides the UV light being generated by individual UVA LED emitter 1080A, UVB LED emitter 1080B, and UVC LED emitter 1080C, the present IPD device 1000 invention can use a specially manufactured at least one multi-die UV LED emitter (not shown) consisting of at least one UVA LED emitter 1080A, at least one UVB LED emitter 1080B, and at least one UVC LED emitter 1080C all in an at least one UV LED package.

Looking at all of the different excitation wavelengths for the various types of smoking particulates including Nicotine, Tar, THC, Polycyclic Aromatic Hydrocarbons, and Humectants Propylene glycol with or without vegetable glycerin; the target UV LED wavelength band ranges should be 365 nm+/−50 nm for the UVA LED(s); 300 nm+/−20 nm for the UVB LED(s); and 240 nm+/−40 nm for the UVC LED(s). This should give a combined total Instant Particulate Detector (IPD) band range of 100 nm to 450 nm coverage from the UV light of the present invention to best excite all possible types of smoking chemicals and particulates presently available. Other combined Instant Particulate Detector (IPD) band ranges with varying UVA, UVB, and UVC wavelength band ranges may be used depending on the type of UV LED emitters that are available from different manufacturers of the UV LEDs.

It will be understood that various changes in the details, materials, types, values, and arrangements of the components that have been described and illustrated in order to explain the nature of this invention may be made by those skilled in the art without departing from the principle and scope of the invention as expressed in the following claims.

We claim:
1. A device for the instant detection of harmful aerosol droplet particles comprising:
a housing;
a UV light source;
a particulate collector;

a background reflector to reflect stray UV light from said UV light source to help fluoresce said harmful aerosol droplet particles on said particulate collector; and a source of power.

2. A device for the instant detection of harmful aerosol droplet particles according to claim 1 further including a Light Guide Plate or LGP to guide direct UV light from said UV light source to said particulate collector.

3. A device for the instant detection of harmful aerosol droplet particles according to claim 1 wherein said UV light source is at least one UV LED emitter.

4. A device for the instant detection of harmful aerosol droplet particles according to claim 3 wherein said at least one UV LED emitter is at least one UVA LED emitter, at least one UVB LED emitter, and at least one UVC LED emitter.

5. A device for the instant detection of harmful aerosol droplet particles according to claim 4 wherein said at least one UVA LED emitter has a wavelength range of about 315 nm to 450 nm, said at least one UVB LED emitter has a wavelength range of about 280 nm to 315 nm, and at least one UVC LED emitter has a wavelength range of about 100 nm to 280 nm.

6. A device for the instant detection of harmful aerosol droplet particles according to claim 3 wherein said at least one UV LED emitter is at least one multi-die UV LED emitter manufactured to emit all wavelength band ranges of said at least one UVA LED emitter, said at least one UVB LED emitter, and said at least one UVC LED emitter.

7. A device for the instant detection of harmful aerosol droplet particles according to claim 6 wherein said at least one UV LED emitter has a wavelength range of about 100 nm to 450 nm.

8. A device for the instant detection of harmful aerosol droplet particles according to claim 1 wherein said UV light source is at least one electroluminescent UV OLED.

9. A device for the instant detection of harmful aerosol droplet particles according to claim 8 wherein said at least one electroluminescent UV OLED has a wavelength range of about 100 nm to 450 nm.

10. A device for the instant detection of harmful aerosol droplet particles according to claim 8 wherein said at least one electroluminescent UV OLED is at least one UVA OLED, at least one electroluminescent UVB OLED, and at least one electroluminescent UVC OLED.

11. A device for the instant detection of harmful aerosol droplet particles according to claim 8 wherein said at least one electroluminescent UV OLED is at least one UVABC OLED, and at least one electroluminescent UVC OLED.

12. A device for the instant detection of harmful aerosol droplet particles according to claim 8 wherein said at least one electroluminescent UV OLED is at least one UVAB OLED, and at least one electroluminescent UVC OLED.

13. A device for the instant detection of harmful aerosol droplet particles according to claim 1 wherein said source of power comes from a battery.

14. A device for the instant detection of harmful aerosol droplet particles according to claim 13 wherein said battery is a rechargeable battery.

15. A device for the instant detection of harmful aerosol droplet particles according to claim 14 wherein said rechargeable battery is a Lithium-Ion battery.

16. A device for the instant detection of harmful aerosol droplet particles according to claim 15 wherein said Lithium-Ion battery is a Lithium-Ion Polymer or LiPo battery.

17. A device for the instant detection of harmful aerosol droplet particles according to claim 13 wherein said battery is a button type battery.

18. A device for the instant detection of harmful aerosol droplet particles according to claim 1 wherein said droplet particles include viral microbe particles.

19. A device for the instant detection of harmful aerosol droplet particles according to claim 1 wherein said droplet particles include bacterial microbe particles.

20. A device for the instant detection of harmful aerosol droplet particles according to claim 1 wherein said droplet particles include smoke particles.

21. A device for the instant detection of harmful aerosol droplet particles according to claim 1 further comprising the disinfection of said harmful aerosol droplet particles using a UVC light source.

22. A device for the instant detection of harmful aerosol droplet particles according to claim 21 wherein said UVC light source is at least one UVC LED emitter.

23. A device for the instant detection of harmful aerosol droplet particles according to claim 22 wherein said at least one UVC LED emitter has a wavelength range of about 100 nm to 280 nm.

24. A device for the instant detection of harmful aerosol droplet particles according to claim 22 wherein said at least one UVC LED emitter has a peak wavelength of about 222 nm.

25. A device for the instant detection of harmful aerosol droplet particles according to claim 22 wherein said at least one UVC LED emitter has a peak wavelength of about 275 nm.

26. A device for the instant detection of harmful aerosol droplet particles according to claim 21 wherein said UVC light source is at least one electroluminescent UVC OLED.

27. A device for the instant detection of harmful aerosol droplet particles according to claim 26 wherein said at least one electroluminescent UVC OLED has a wavelength range of about 200 nm to 280 nm.

28. A device for the instant detection of harmful aerosol droplet particles according to claim 26 wherein said at least one electroluminescent UVC OLED has a peak wavelength of about 222 nm.

29. A device for the instant detection of harmful aerosol droplet particles according to claim 26 wherein said at least one electroluminescent UVC OLED has a peak wavelength of about 275 nm.

30. A device for the instant detection of harmful aerosol droplet particles according to claim 1 further comprising an audio alarm to supplement the detection of harmful aerosol droplet particles.

31. A device for the instant detection of harmful aerosol droplet particles according to claim 30 wherein said audio alarm is generated by a tiny speaker.

32. A device for the instant detection of harmful aerosol droplet particles according to claim 1 further comprising at least one switch to communicate said source of power to said UV light source.

33. A device for the instant detection of harmful aerosol droplet particles according to claim 32 wherein said at least one switch is used to set the device in detection mode or in disinfection mode.

34. A device for the instant detection of harmful aerosol droplet particles according to claim 1 for use with personal protective equipment.

35. A device for the instant detection of harmful aerosol droplet particles according to claim 34 wherein said personal protective equipment includes safety googles.

36. A device for the instant detection of harmful aerosol droplet particles according to claim 34 wherein said personal protective equipment includes face masks.

37. A device for the instant detection of harmful aerosol droplet particles according to claim 34 wherein said personal protective equipment includes face shields.

38. A device for the instant detection of harmful aerosol droplet particles according to claim 34 wherein said personal protective equipment includes safety gloves.

39. A device for the instant detection of harmful aerosol droplet particles according to claim 34 wherein said personal protective equipment includes arm sleeves.

40. A device for the instant detection of harmful aerosol droplet particles according to claim 34 wherein said personal protective equipment includes head hoods.

41. A device for the instant detection of harmful aerosol droplet particles according to claim 34 wherein said personal protective equipment includes solid hairnets.

42. A device for the instant detection of harmful aerosol droplet particles according to claim 34 wherein said personal protective equipment includes body coveralls.

43. A device for the instant detection of harmful aerosol droplet particles according to claim 34 wherein said personal protective equipment includes body gowns.

44. A device for the instant detection of harmful aerosol droplet particles according to claim 1 made in the shape of a round circular dot.

45. A device for the instant detection of harmful aerosol droplet particles according to claim 1 made in the shape of a linear rectangular strip.

46. A portable device with a power supply cord and plug for the instant detection and disinfection of harmful aerosol droplet particles comprising:
- a housing with a top and a bottom;
- at least one UVA LED emitter;
- at least one UVB LED emitter;
- at least one UVC LED emitter;
- a particulate collector;
- a background reflector to reflect stray UV light from said at least one UVA LED emitter, said at least one UVB LED emitter; and at least one UVC LED emitter to help fluoresce said harmful aerosol droplet particles on said particulate collector; and
- using said at least one UVC LED to disinfect said harmful aerosol droplet particles collected on said particulate collector.

47. A device for the instant detection of harmful aerosol droplet particles according to claim 46 further comprising at least one switch to communicate power to said device.

48. A device for the instant detection of harmful aerosol droplet particles according to claim 47 wherein said at least one switch is used to set the device in detection mode or in disinfection mode.

49. A device for the instant detection of harmful aerosol droplet particles according to claim 46 wherein said droplet particles include viral microbe particles.

50. A device for the instant detection of harmful aerosol droplet particles according to claim 46 wherein said droplet particles include bacterial microbe particles.

51. A device for the instant detection of harmful aerosol droplet particles according to claim 46 wherein said droplet particles include smoke particles.

52. A device for the instant detection of harmful aerosol droplet particles according to claim 46 wherein said particle collector is a personal protective equipment.

53. A device for the instant detection of harmful aerosol droplet particles according to claim 52 wherein said personal protective equipment includes safety googles.

54. A device for the instant detection of harmful aerosol droplet particles according to claim 52 wherein said personal protective equipment includes face masks.

55. A device for the instant detection of harmful aerosol droplet particles according to claim 52 wherein said personal protective equipment includes face shields.

56. A device for the instant detection of harmful aerosol droplet particles according to claim 52 wherein said personal protective equipment includes safety gloves.

57. A device for the instant detection of harmful aerosol droplet particles according to claim 52 wherein said personal protective equipment includes arm sleeves.

58. A device for the instant detection of harmful aerosol droplet particles according to claim 52 wherein said personal protective equipment includes head hoods.

59. A device for the instant detection of harmful aerosol droplet particles according to claim 52 wherein said personal protective equipment includes solid hairnets.

60. A device for the instant detection of harmful aerosol droplet particles according to claim 52 wherein said personal protective equipment includes body coveralls.

61. A device for the instant detection of harmful aerosol droplet particles according to claim 52 wherein said personal protective equipment includes body gowns.

62. A device for the instant detection of harmful aerosol droplet particles according to claim 46 wherein said particle collector is an object.

63. A device for the instant detection of harmful aerosol droplet particles comprising:
- a housing;
- a multi-band UVA, UVB, and UVC light source;
- a particulate collector;
- a background reflector to reflect stray multi-band UVA, UVB, and UVC light to said particulate collector; and
- at least one replaceable battery to provide power to said device.

64. A device for the instant detection of harmful aerosol droplet particles according to claim 63 made in the shape of a round circular dot.

65. A device for the instant detection of harmful aerosol droplet particles according to claim 63 made in the shape of a linear rectangular strip.

* * * * *